(12) United States Patent
Chahine et al.

(10) Patent No.: US 11,891,733 B2
(45) Date of Patent: Feb. 6, 2024

(54) SYSTEM FOR AN INSULATED TEMPERATURE SENSOR INCORPORATED IN A BASE FABRIC LAYER

(71) Applicant: MYANT INC., Toronto (CA)

(72) Inventors: Tony Chahine, Toronto (CA); Ladan Eskandarian, Toronto (CA); Godfried Edelman, Toronto (CA)

(73) Assignee: MYANT INC., Toronto (CA)

( * ) Notice: Subject to any disclaimer, the term of this patent is extended or adjusted under 35 U.S.C. 154(b) by 430 days.

(21) Appl. No.: 17/292,678

(22) PCT Filed: Nov. 12, 2018

(86) PCT No.: PCT/IB2018/058878
§ 371 (c)(1),
(2) Date: May 10, 2021

(87) PCT Pub. No.: WO2020/099907
PCT Pub. Date: May 22, 2020

(65) Prior Publication Data
US 2022/0003613 A1 Jan. 6, 2022

(51) Int. Cl.
*D04B 21/20* (2006.01)
*D03D 15/533* (2021.01)
(Continued)

(52) U.S. Cl.
CPC ............. *D04B 21/20* (2013.01); *D03D 15/25* (2021.01); *D03D 15/533* (2021.01); *D04B 1/14* (2013.01);
(Continued)

(58) Field of Classification Search
CPC . D04B 1/14; D04B 1/22; D04B 1/225; D04B 1/12; D04B 7/32; D04B 9/16;
(Continued)

(56) References Cited

U.S. PATENT DOCUMENTS 5,118,569 A * 6/1992 Kuroda .................... D04B 1/14
442/310
6,854,296 B1 * 2/2005 Miller, III ................ D04B 1/22
66/196
(Continued)

FOREIGN PATENT DOCUMENTS

| GB | 1361358 A | 7/1974 |
|---|---|---|
| WO | 2009001108 A1 | 12/2008 |
| WO | 2017063994 A1 | 4/2017 |

OTHER PUBLICATIONS

Japan Patent Office, Notice of Allowance for Japanese Application No. 2021-525262, dated Jul. 12, 2022.
(Continued)

*Primary Examiner* — Danny Worrell
(74) *Attorney, Agent, or Firm* — Norton Rose Fulbright Canada LLP

(57) ABSTRACT

A system of fibre based temperature sensor integrated into abase fabric layer for a garment, the system comprising: a set of wall fibres interlaced with one another to form a first wall structure defining a first cavity along a length and a second wall structure defining a second cavity along the length, the set of wall fibres comprising nonconductive material; at least one conductive fibre miming along the length within each cavity, such that the set of wall fibres of the wall structures encloses each at least one conductive fibre in order to electrically insulate each at least one conductive fibre from an environment along the length external to the cavities; and a set of base fibres interlaced with one another to form the base fabric layer.

16 Claims, 16 Drawing Sheets

(51) Int. Cl.
   *D03D 15/25*    (2021.01)
   *D04B 1/14*     (2006.01)
   *G01K 7/16*     (2006.01)
   *D04B 1/22*     (2006.01)

(52) U.S. Cl.
   CPC ............... *D04B 1/22* (2013.01); *G01K 7/16* (2013.01); *D10B 2101/20* (2013.01); *D10B 2403/02431* (2013.01)

(58) Field of Classification Search
   CPC ........ D04B 9/44; D04B 21/08; D04B 21/205; D04B 23/10; D04B 21/20; D03B 15/533; D03B 15/25; D10B 2403/02431
   See application file for complete search history.

(56) References Cited

U.S. PATENT DOCUMENTS

| | | | |
|---|---|---|---|
| 6,941,775 B2 | 9/2005 | Sharma | |
| 10,945,663 B2 * | 3/2021 | Bozkurt | ............ G01N 27/048 |
| 2006/0070676 A1 * | 4/2006 | Blackmore | .............. D04C 1/02 |
| | | | 156/95 |
| 2009/0013728 A1 * | 1/2009 | Dias | .......... D04B 1/14 |
| | | | 66/171 |
| 2012/0246973 A1 * | 10/2012 | Dua | .......... A43B 23/0255 |
| | | | 36/83 |
| 2014/0180624 A1 | 6/2014 | Nikonov et al. | |
| 2015/0305676 A1 * | 10/2015 | Shoshani | ............. A61B 5/6805 |
| | | | 66/202 |
| 2019/0350303 A1 * | 11/2019 | Huffa | ....... D04B 1/22 |
| 2020/0207057 A1 * | 7/2020 | Bowles | ..................... B32B 5/26 |
| 2021/0172096 A1 * | 6/2021 | Kondo | ................. D03D 15/497 |
| 2022/0003613 A1 * | 1/2022 | Chahine | ................... G01K 7/16 |
| 2022/0007986 A1 * | 1/2022 | Chahine | ................ A61B 5/304 |

OTHER PUBLICATIONS

PCT, Written Opinion and International Search Report of International Application No. PCT/IB2018/058878, dated Sep. 13, 2019.
European Patent Office, Extended European Search Report for European Application No. EP 18 94 0173, dated May 30, 2022.

* cited by examiner

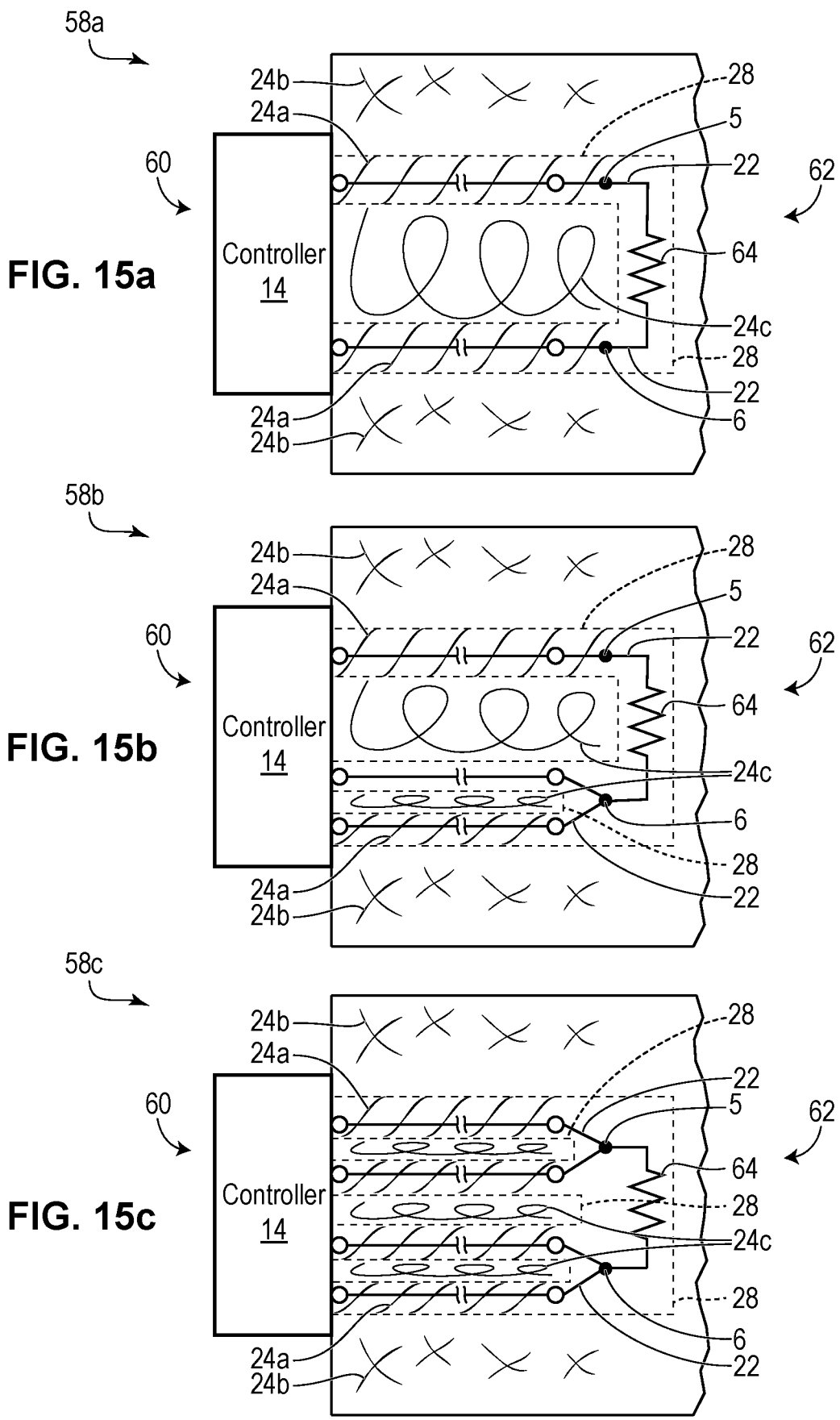

SYSTEM FOR AN INSULATED TEMPERATURE SENSOR INCORPORATED IN A BASE FABRIC LAYER

FIELD

The present disclosure relates to insulated conductors for smart textiles.

BACKGROUND

The protection of conductive fibres present in smart technology textiles can be problematic due to electrical insulation, thermal protection, as well as train and stretch protection. It is recognised that conductive fibres present in the interlaced set of fibres of a textile body require shielding from inadvertent contact from adjacent conductive fibres as well as electrically conductive objects (e.g. metallic objects handled by a wearer of the textile) external to the textile. In particular, conductive fibres (e.g. metal wire) need to be selectively shielded from shorts, strain, stretch and direct contact with elements external to the textile.

In particular, it is desirable to reduce costs associated with the manufacture and assembly of smart textiles, especially in which the conductive fibres are interlaced directly into the body of the textile as the set of textile fibres is being manufactured, e.g. also referred to as interlaced (e.g. knitted) on demand.

In terms of fibre-based temperature sensors, the physical length of the conductive fibres is used to measure the temperature, based on the temperature measurement being proportional to the electrical resistance of the conductive fibres making up the fibre based temperature sensor. It is recognised that a number of factors can influence, i.e. undesirably vary, the current resistance of the conductive fibres. For example, any change in length/cross sectional area of the conductive fibres would result in a change in the electrical resistance. For example, exposure to moisture of the conductive fibres would result in a change in the electrical resistance. This is especially important for conductive yarns as textiles/garments can be exposed to environmental moisture sources as well as moisture from the user's body directly. Plastic insulation applied to the exterior surface of the wires works well in non-textile applications. However in textile/garment applications, plastic coated wires are discouraged due to their relative inflexibility in comparison to other non-conductive fibres making up the textile/garment, as well as an unsightly appearance of the plastic coated wires in comparison to other non-conductive fibres making up the textile/garment. For example, exposure to heat (e.g. body heat) of the textile/garment user can also impact the resistance of the conductive fibres of the temperature sensor.

The protection of conductive fibres in textiles is particularly important, as "smart" garments utilize multiple paths of conductive fibres to carry power and signals to different locations on the textile body of the garment.

SUMMARY

It is an object of the present invention to provide a fibre-based temperature sensor to obviate or mitigate at least one of the above presented disadvantages.

A first aspect provided is a system for a fibre based temperature sensor integrated into a base fabric layer for a textile, the system comprising: a first set of wall fibres interlaced with one another to form a first wall structure defining a first cavity along a length, the first set of wall fibres comprising nonconductive material; at least one conductive first fibre running along the length within the first cavity, such that the first set of wall fibres of the first wall structure encloses the at least one conductive first fibre in order to electrically insulate the at least one conductive first fibre from an environment along the length external to the first cavity; a second set of wall fibres interlaced with one another to form a second wall structure defining a second cavity along the length, the second set of wall fibres comprising nonconductive material, the wall structures adjacent to one another along the length; at least one conductive second fibre running along the length within the second cavity, such that the second set of wall fibres of the second wall structure encloses the at least one conductive second fibre in order to electrically insulate the at least one conductive second fibre from the environment along the length external to the second cavity, wherein the first wall structure and the second wall structure are adjacent and interconnected to one another; a set of base fibres interlaced with one another to form the base fabric layer, the base fabric layer having a first side adjacent with a first fibred interconnection to the first wall structure and a second side adjacent with a second fibered interconnection to the second wall structure, the first fibered interconnection opposed to the second fibred interconnection, the first side and the second side forming a surface of the base fabric layer such that the first wall structure and the second wall structure are interposed between the first and second sides, the first fibred interconnection and the second fibred interconnection forming part of a structural fabric integrity of the set of first wall fibres and the set of second wall fibres respectively in combination with a structural fabric integrity of the set of base fibres; wherein damage to fibres of at least one of the first fibred interconnection results in destruction of the structural fabric integrity of the set of first wall fibres or the second fibred interconnection results in destruction of the structural fabric integrity of the set of second wall fibres, in combination with the structural fabric integrity of the set of base fibres.

A second aspect provided is a method for manufacturing fibre based temperature sensor integrated into a base fabric layer for a textile, the method comprising the steps of: interlacing a set of wall fibres with one another to form a first wall structure defining a first cavity along a length and a second wall structure defining a second cavity along the length, the set of wall fibres comprising nonconductive material, the wall structures adjacent to one another along the length; positioning at least one conductive fibre running along the length within each of the first cavity and the second cavity, such that the set of wall fibres of the wall structures enclose each of the at least one conductive fibre in order to electrically insulate each of the at least one conductive fibre from an environment along the length external to the cavities; interlacing a set of base fibres with one another to form the base fabric layer; and interlacing a first fibred interconnection and a second fibred interconnection between the base fabric layer and the first and second wall structures, the base fabric layer having a first side adjacent with the first fibred interconnection to the first wall structure and a second side adjacent with the second fibered interconnection to the second wall structure, the first fibered interconnection opposed to the second fibred interconnection, the first side and the second side forming a surface of the base fabric layer such that the first and second wall structures are interposed between the first and second sides, the first fibred interconnection and the second fibred interconnection forming part of a structural fabric integrity of the set of wall fibres and a structural fabric integrity of the set of base fibres; wherein subsequent damage to fibres of at least one of the first fibred interconnection or the second fibred interconnection results in destruction of the structural fabric integrity of the set of wall fibres and the structural fabric integrity of the set of base fibres.

A third aspect provided is a method for manufacturing fibre based temperature sensor integrated into a base fabric layer for a textile, the method comprising the steps of: interlacing a set of wall fibres with one another to form a first wall structure defining a first cavity along a length and a second wall structure defining a second cavity along the length, the set of wall fibres comprising nonconductive material, the wall structures adjacent to one another along the length; positioning at least one conductive fibre running along the length within each of the first cavity and the second cavity, such that the set of wall fibres of the wall structures enclose each of the at least one conductive fibre in order to electrically insulate each of the at least one conductive fibre from an environment along the length external to the cavities; interlacing a set of base fibres with one another to form the base fabric layer and connected to the pair of first and second wall structures.

The base fabric layer with interlacing a first fibred interconnection and a second fibred interconnection between the base fabric layer and the first and second wall structures, the base fabric layer having a first side adjacent with the first fibred interconnection to the first wall structure and a second side adjacent with the second fibered interconnection to the second wall structure, the first fibered interconnection opposed to the second fibred interconnection, the first side and the second side forming a surface of the base fabric layer such that the first and second wall structures are interposed between the first and second sides, the first fibred interconnection and the second fibred interconnection forming part of a structural fabric integrity of the set of wall fibres and a structural fabric integrity of the set of base fibres; wherein subsequent damage to fibres of at least one of the first fibred interconnection or the second fibred interconnection results in destruction of the structural fabric integrity of the set of wall fibres and the structural fabric integrity of the set of base fibres.

A further aspect provided is a system for a fibre based temperature sensor integrated into a base fabric layer for a textile, the system comprising: a first set of wall fibres interlaced with one another to form a first wall structure defining a first cavity along a length, the first set of wall fibres comprising nonconductive material; at least one conductive first fibre running along the length within the first cavity, such that the first set of wall fibres of the first wall structure encloses the at least one conductive first fibre in order to electrically insulate the at least one conductive first fibre from an environment along the length external to the first cavity; a second set of wall fibres interlaced with one another to form a second wall structure defining a second cavity along the length, the second set of wall fibres comprising nonconductive material, the wall structures adjacent to one another along the length; at least one conductive second fibre running along the length within the second cavity, such that the second set of wall fibres of the second wall structure encloses the at least one conductive second fibre in order to electrically insulate the at least one conductive second fibre from the environment along the length external to the second cavity, wherein the first wall structure and the second wall structure are adjacent and interconnected to one another; and a set of base fibres interlaced with one another to form the base fabric layer, such that the first wall structure and the second wall structure are interposed between first and second sides of the base fabric layer.

BRIEF DESCRIPTION OF THE DRAWINGS

The foregoing and other aspects will now be described by way of example only with reference to the attached drawings, in which:

FIG. 14b is an operational example of stretch experienced by the fibre based temperature sensor of FIG. 14a;

FIGS. 15a,b,c are different further embodiments of the fibre based temperature sensor of FIG. 14a; and FIGS. 16,17,18,19 are still further embodiments of the fibre based temperature sensor of FIG. 14a.

DETAILED DESCRIPTION

Figure 1:
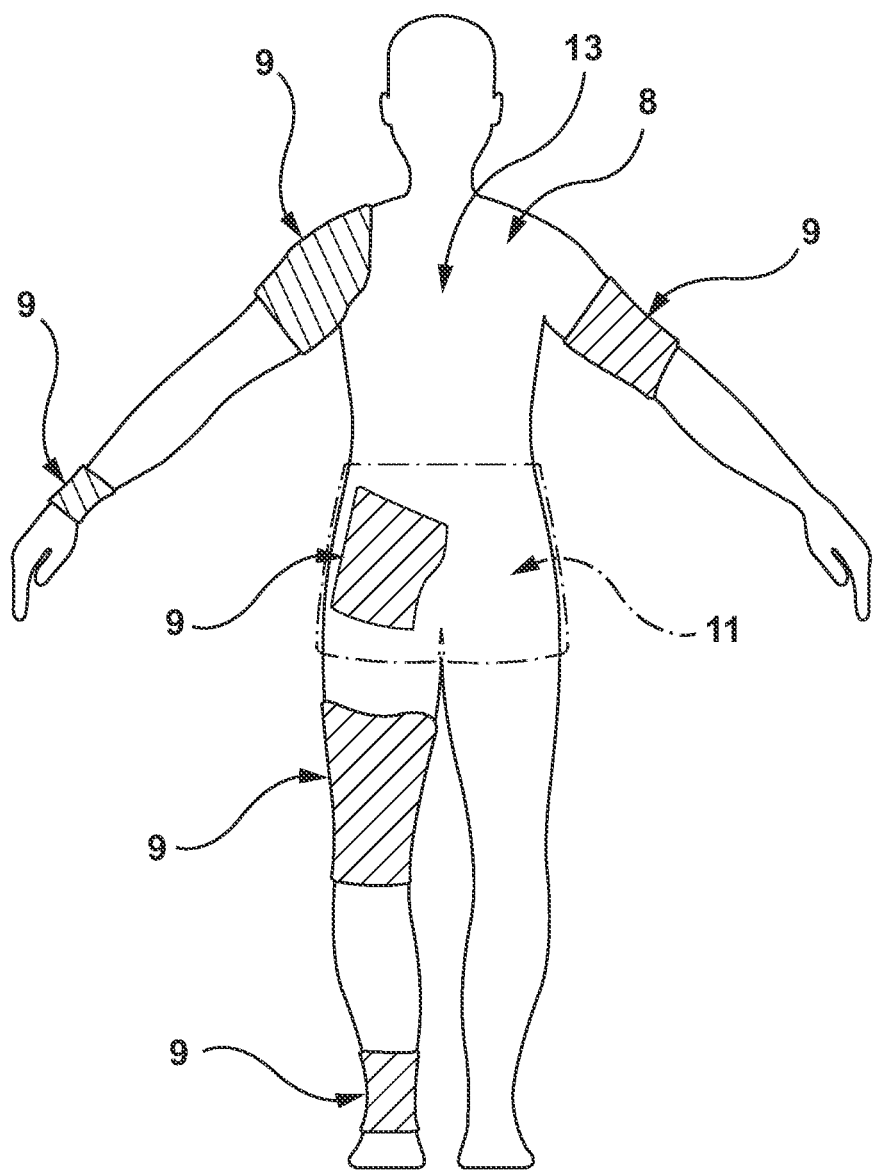
FIG. 1 is system view of garment examples for wearing on a body of a wearer.
Figure 2:
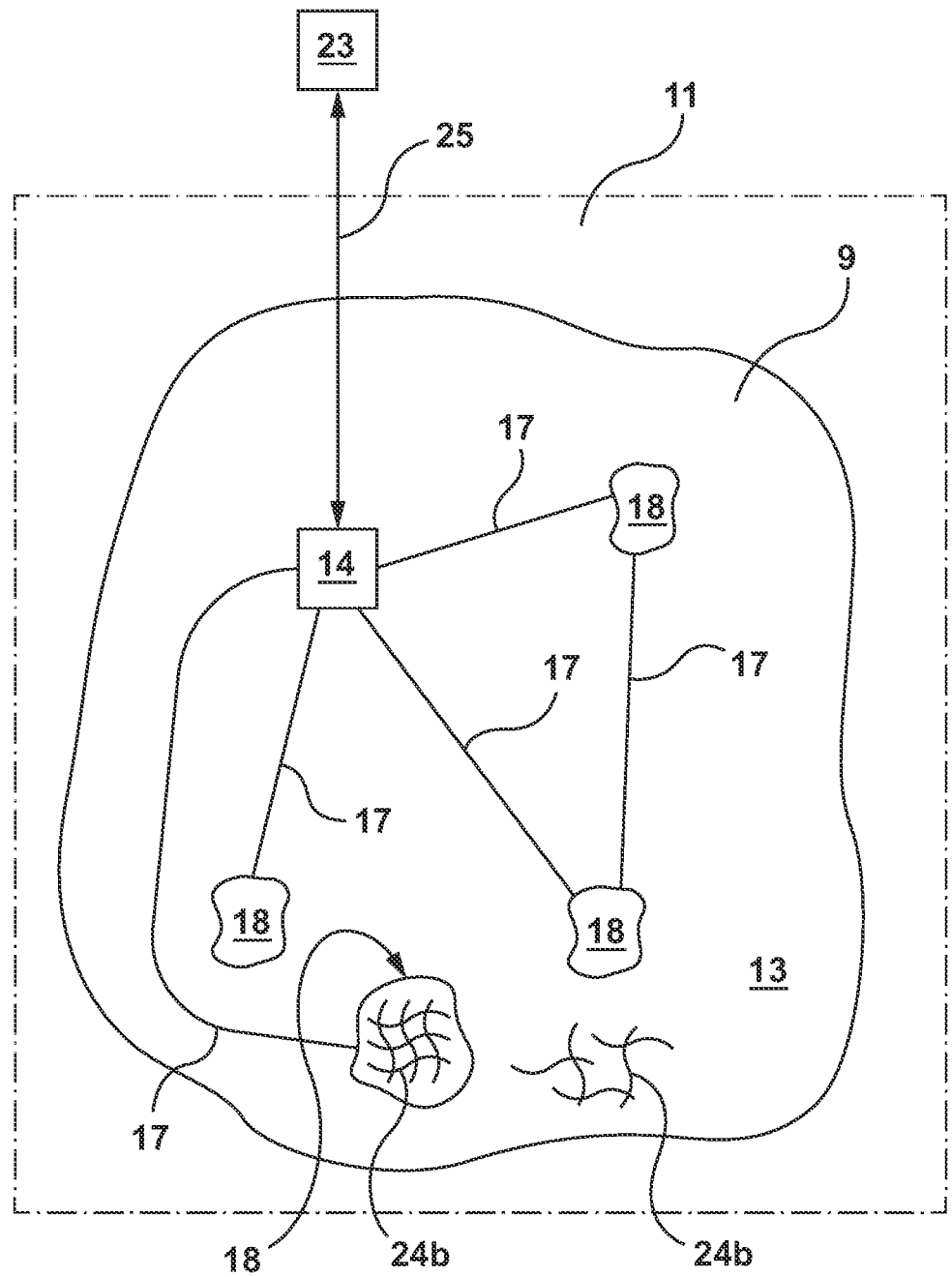
FIG. 2 is an exemplary view of a textile computing platform of the garment of FIG. 1 incorporated into an article of clothing including a variety of sensors/actuators and conductive pathways.

Referring to FIG. 1, shown is a body 8 of a wearer for wearing one or more textile based computing platforms 9 positioned about one or more regions (e.g. knee, ankle, elbow, wrist, hip, shoulder, neck, etc.) of the body 8. For sake of simplicity, textile based computing platforms 9 can also be referred to as textile computing platforms 9. For example, the textile computing platforms 9 can also be referred to as a wrist sleeve 9, a knee sleeve 9, a shoulder sleeve 9, an ankle sleeve 9, a hip sleeve 9, a neck sleeve 9, etc. It is also recognized that the textile computing platform 9 can be incorporated as part of a larger garment 11 (e.g. a pair of briefs 11 as shown in ghosted view for demonstration purposes only). It is recognized that the garment 11 could also be a shirt, pants, body suit, as desired. As such, a fabric/textile body 13 of the garment 11 can be used to position the textile computing platform 9 for selected areas of the body 8. In other words, the textile computing platform 9 contains a number of textile computing components, e.g. sensors/actuators 18, electronic circuits 17, controller 14—see FIG. 2, which are all incorporated into or otherwise mounted on a fabric/textile body 13 of the garment 11.

It is also recognised that the textile computing platform 9 can be incorporated into a textile 9 (e.g. a fabric sheet, a covering, or other fabric structure) that is not worn by the body 8, rather is positioned adjacent to the body 8. Examples of the textile 9 can include bedsheets, seat coverings (e.g. car seat), etc.

Referring again to FIGS. 1 and 2, the textile computing platform 9 is integrated with the textile/fabric body 13 (e.g. a plurality of fibres/threads/yarn interlaced as woven and/or knitted, as desired). The textile computing platform 9 has the controller 14 for sending/receiving signals to one or more sensors/actuators 18 distributed about the body 13. The shape of the sensors/actuators 18 can be elongate (e.g. as a strip extending in a preferred direction) or can extend as a patch in a plurality of directions (e.g. extend side to side and end to end). The signals are transmitted between the sensors/actuators 18 and the controller 14 via one or more electronic circuits 17 connecting the controller 14 to each of the sensors/actuators 18. It is also recognized that the electronic circuits 17 can also be between individual pairs of the sensors/actuators 18, as desired. As further described below, the sensors/actuators 18 can be textile based, i.e. incorporated via interlaced (e.g. knitting, weaving) as integral to the material structural integrity of the fabric layer of the body 13 (formed as a plurality of interlaced threads of electrically conductive and optionally non-conductive properties). Further, the electronic circuits 17 (e.g. electrically conductive threads) can also be incorporated/interlaced (e.g. knitting, weaving, etc.) into/with the adjacent fabric layer of the body 13 (also comprising a plurality of interlaced threads/fibres). The controller 14, further described below, can include a network interface (e.g. wireless or wired) for communicating with a computing device 23 (e.g. smart phone, tablet, laptop, desktop, etc.) via a network 25.

Figure 3:
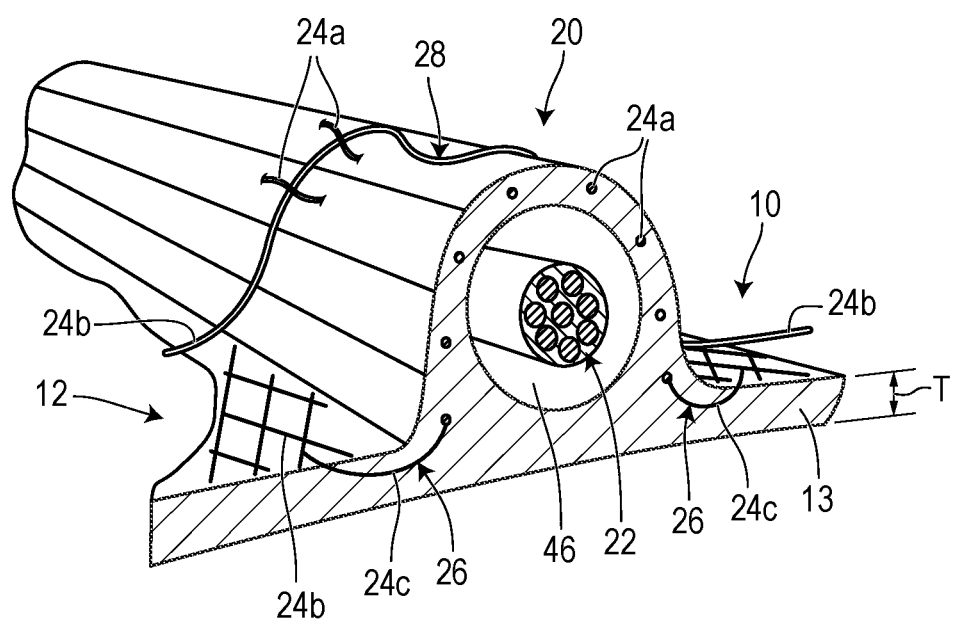
FIG. 3 shows an embodiment of a fibre based temperature sensor integrated directly into the interlacing of the fibres making up the body of the textile computing platform shown in FIG. 2.

As shown in FIG. 3, the fabric layer of the body 13 has a first side 10 and a second side 12, such that the sides 10, 12 are opposed to one another with respect to an intervening insulated conductor 20. Preferably the side 10 and the side 12 of the fabric layer of the body 13 are situated in the same plane (e.g. a flat or curved fabric surface of thickness T—uniform or varied) in a composition of the textile computing platform 9 of the garment 11 (see FIG. 2). It is recognised that the sensors/actuators 18 of the textile based computing platform 9 can be formed as integral components of the interlacing of the fibres making up the body 13. The fabric of the body 13 can be comprised of interlaced resilient fibres 24*b* (e.g. stretchable natural and/or synthetic material and/or a combination of stretchable and non-stretchable materials, recognizing that at least some of the fibres comprising the sensors/actuators 18 are electrically conductive, i.e. metallic). It is recognised that FIGS. 3 and 5-12 show one wall structure 28 of one insulted conductor 20 for the temperature sensor for clarity/demonstration purposes, by example only. As such, FIGS. 14*a,b*, 15*a,b,c*, 16, 17, 18, 19 all show multiple insulated conductors 20 adjacent to one another using the interlacing construction techniques of the wall structures 28 described in FIGS. 3 and 5-13 that are compatible for multiple adjacent wall structures 28 as shown.

Referring to FIG. 3, shown is an example insulated conductor 20 for one or more conductive fibres 22 (e.g. thread(s), yarn(s), etc.). The conductive fibre(s) 22 can be, for example, the electronic circuit 17 as described with reference to FIG. 2. The insulated conductor 20 is comprised of a plurality of insulative (i.e. non-conductive) interlaced fibres 24*a* (e.g. woven, and/or knitted fibres 24*a* with respect to one another) in a wall structure 28, such that the interlaced fibres 24*a* are connected 26 with respect to one or more fibres 24*b* making up the fabric layer of the body 13. The fibres 24*a* are formed as (e.g. at least a portion of) the wall structure 28 (e.g. tube) surrounding the conductive fibre(s) 22. The fibre(s) 24*a* can be referred to as wall fibre(s) 24*a*, the fibre(s) 24*b* can be referred to as base fibre(s) 24*a* and any optional individual fibres 24*c* can be referred to as connection fibre(s) 24*c*.

In terms of being connected 26, this can mean that, for example, the set of fibres 24*a* can contain or otherwise be interlaced with one or more of the fibres 24*b* (e.g. the fibre 24*b* is integral with/common to both the fabric layer of the body 13 on either side 10, 12 of the wall structure 28, and the wall structure 28 (one or more sides 30, 32, 34 as described below)—see FIG. 3). Alternatively, the fibre(s) 24*a* could be interlaced (i.e. connected 26) to the fibre(s) 24*b* via one or more intervening fibre(s) 24*c* interlacing the fibre(s) 24*a* with the fibre(s) 24*b*—see FIG. 5, such that the intervening fibre(s) 24*c* are each on one of the sides 10,12 but not both. This is compared to the fibre(s) 24*b* in the set of fibres 24*a*, as the connecting 26 mechanism, which extend from one side 10 to the other side 12 via the wall structure 28. Further, it is recognised that the term connected 26 can include both the presence of fibres 24*b* as well as fibres 24*c*, in combination. Accordingly, in terms of the connection 26 involving the connection fibres 24*c*, the pattern of interlacing between the fibres 24*a,b,c* can be knitting or waving, for example. As such, the connection 26 can be formed by interlacing the fibres 24*c* both with adjacent fibres 24*b* in the base fabric layer 13 and with adjacent fibres 24*a* in the wall structure 28. As such, the connection 26 can be formed by interlacing the fibre(s) 24*b* in the base fabric layer 13 (e.g. extending form one side 10 to the other side 12) with adjacent fibres 24*a* in the wall structure 28.

In any event, it is recognised that at least a portion of the fibres 24*b* in the wall structure 28 and/or the fibres 24*c* in the wall structure 28 are included as an interlaced component providing structural integrity of the fabric layer of the body 13, as the fibres 24*b* and/or 24*c* are incorporated (i.e. interlaced) into the wall structure 28 and the fabric layer of the body 13 at the same time of interlacing (e.g. weaving, knitting) of the textile computing platform 9 of the garment 11. In other words, removing the fibre(s) 24*b*,24*c* connecting 26 the fibres 24*a* to the fabric layer of the body 13 would destroy the structural integrity of the interlacing of the fibres 24*b* with one another in the fabric layer of the body 13, as there are fibre(s) 24*b*,24*c* common to both the base fabric layer of the body 13 and the wall structure 28.

Figure 4:
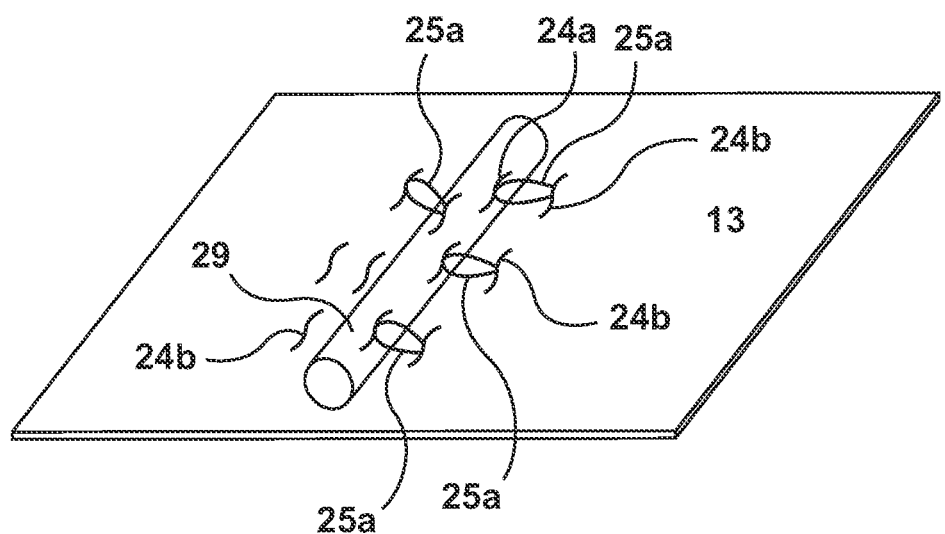
FIG. 4 shows a further example applications of the fibre based temperature sensor of FIG. 3.
Figure 5:
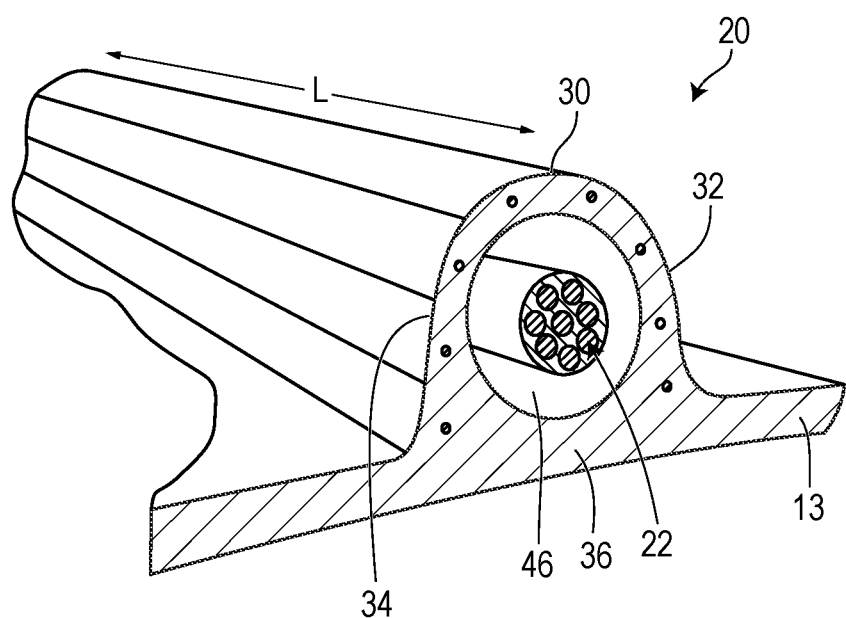
FIG. 5 shows a front perspective view of an embodiment of the fibre based temperature sensor of FIG. 3.

The connected 26 examples shown in FIG. 3 of fibre(s) 24*b,c* are differentiated from deemed prior art embroidery example shown in FIG. 4, such that fibres 25*a* connecting an independent knit structure 29 to the base fabric layer 13 are simply contained/separate fibres to that of the interlaced fibres 24*b* of the fabric layer of the body 13 and the interlaced fibres 24*a* making up the independent knit structure 29 (e.g. at least of the sides 30, 32, 34), such that removal (e.g. severing i.e. breaking the connection 25*a*) of the fibres 25*a* (applied via embroidery techniques for example) from between independent knit structure 29 and the fabric layer of the body 13 would not result in destroying/compromising the structural integrity of the interlacing between the respective set of fibres 24*a* in the sides 30,32,34 as well would not destroy/compromise the structural integrity of the interlacing between the fibres in the respective set of fibres 24*b* in the fabric layer of the body 13. It is recognised that in terms of embroidery, the process of applying the fibres 25*a* in FIG. 4 can be done after (e.g. separate to) the process of manufacturing (e.g. weaving, knitting) both individually the fabric layer of the body 13 and the independent knit structure 29. This separate process of embroidering, as shown in FIG. 4, is compared to the simultaneous interlacing process of forming the fabric layer of the body 13 along with the interconnections 26 and the wall structure 28 containing the conductive fibre(s) 22 shown in FIG. 3.

In comparison to the prior art example shown in FIG. 4, the set of fibres 24*a,b,c* shown in FIG. 3 do advantageously provide for a sharing of the structural integrity of the interlacing in the wall structure 28. In other words, severing or otherwise breaking or trying to remove any fibres (in the wall structure 28 and/or in the base fabric layer 13 adjacent to the wall structure 28) of a pair of the types of fibres 24*a,b,c* would result in compromising or otherwise impacting detrimentally the structural integrity of the interlaced fibres making up of the wall structure 28 and/or the adjacent base fabric layer 13.

For example, in one embodiment the base fibre(s) 24*b* are included with the wall fibre(s) 24*a* as the pair of fibre types interlaced with one another in the wall structure 28 so as to cooperatively provide for the structural integrity of the interlacing network of the fibres 24*a,b* making up the wall structure 28. Thus, it is recognised that any breaking/severing of fibre(s) 24*a* and/or 24*b* present in (and/or adjacent to) the wall structure 28 would compromise the structural integrity (e.g. unravelling of the wall structure 28 and/or the base fabric layer 13 adjacent to the wall structure 28), which would be undesirably facilitated in subsequent "wear and tear" (wearing and/or cleaning of the garment/textile 11) of the textile computing platform 9 (i.e. containing the base fabric layer 13 and the wall structure(s) 28). As the desired continued integrity/attachment of the wall structure 28 to the base fabric layer 13 is considered important (e.g. in order to provide for the desired insulative properties for the conductive fibre 22), as well as the desired integrity of the base fabric layer 13 (e.g. providing the contextual structure of the complete garment/textile 11) is considered important, the ability of the selected pair of fibre 24*a,b* types to cooperate and maintain the structural integrity of both the wall structure 28 and the base fabric layer 13 in the vicinity of the base fabric layer 13 is important.

For further example, in another embodiment the connection fibre(s) 24*c* are included with the wall fibre(s) 24*a* as the pair of fibre types interlaced with one another in the wall structure 28 so as to cooperatively provide for the structural integrity of the interlacing network of the fibres 24*a,c* making up the wall structure 28. It is also deemed that the connection fibre(s) 24*c* are at the same time also interlaced with the base fibre(s) 24*b* and thus also contribute to the structural integrity of the fibre interlacing making up of the base fabric layer 13. Thus, it is recognised that any breaking/severing of fibre(s) 24*a* and/or 24*c* present in (and/or adjacent to) the wall structure 28 would compromise the structural integrity (e.g. unravelling of the wall structure 28 and/or the base fabric layer 13 adjacent to the wall structure 28), which would be undesirably facilitated in subsequent "wear and tear" (wearing and/or cleaning of the garment/textile 11) of the textile computing platform 9 (i.e. containing the base fabric layer 13 and the wall structure(s) 28). As the desired continued integrity/attachment of the wall structure 28 to the base fabric layer 13 is considered important (e.g. in order to provide for the desired insulative properties for the conductive fibre 22), as well as the desired integrity of the base fabric layer 13 (e.g. providing the contextual structure of the complete garment/textile 11) is considered important, the ability of the selected pair of fibre 24*a,c* types to cooperate and maintain the structural integrity of both the wall structure 28 and the base fabric layer 13 in the vicinity of the base fabric layer 13 is important.

For further example, in another embodiment the connection fibre(s) 24*c* and the base fibre(s) 24*b* are included with the wall fibre(s) 24*a* as the pairs of fibre types interlaced with one another in the wall structure 28 so as to cooperatively provide for the structural integrity of the interlacing network of the fibres 24*a,b,c* making up the wall structure 28. It is also deemed that the connection fibre(s) 24*c* are at the same time also interlaced with the base fibre(s) 24*b* and thus also contribute to the structural integrity of the fibre interlacing making up of the base fabric layer 13. Thus, it is recognised that any breaking/severing of fibre(s) 24*a*, 24*b* and/or 24*c* present in (and/or adjacent to) the wall structure 28 would compromise the structural integrity (e.g. unravelling of the wall structure 28 and/or the base fabric layer 13 adjacent to the wall structure 28), which would be undesirably facilitated in subsequent "wear and tear" (wearing and/or cleaning of the garment/textile 11) of the textile computing platform 9 (i.e. containing the base fabric layer 13 and the wall structure(s) 28). As the desired continued integrity/attachment of the wall structure 28 to the base fabric layer 13 is considered important (e.g. in order to provide for the desired insulative properties for the conductive fibre 22), as well as the desired integrity of the base fabric layer 13 (e.g. providing the contextual structure of the complete garment/textile 11) is considered important, the ability of the selected pairs of fibre 24*a,b,c* types to cooperate and maintain the structural integrity of both the wall structure 28 and the base fabric layer 13 in the vicinity of the base fabric layer 13 is important.

Figure 6:
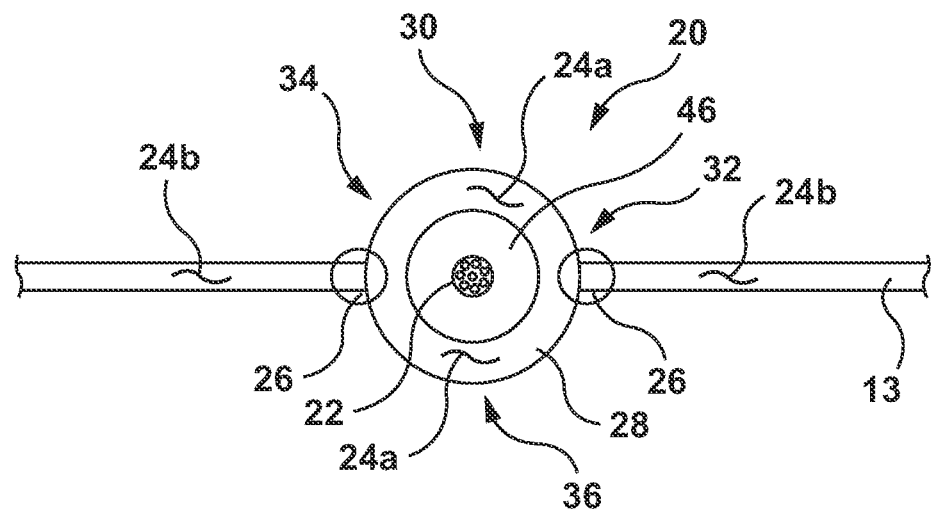
FIG. 6 shows a cross sectional view of a further embodiment of the fibre based temperature sensor of FIG. 3.

Referring again to FIGS. 3 and 5, shown is the example embodiment in which the wall structure 28 comprises mainly the interlaced fibres 24*a* making up a first side 30, a second side 32 and a third side 34 to partially surround the conductive fibre(s) 22. A fourth side 36 of the wall structure 28 can be formed of the fabric layer of the body 13 including predominantly or completely the fibres 24*b*, thus providing for the insulative structure 20 having the four sides 30, 32, 34, 36 to completely encapsulate the conductive fibre(s) 22 along a length L of the fibre(s) 22. Alternatively, as shown in FIG. 6, a further example embodiment of the wall structure 28 comprises mainly the interlaced fibres 24*a* making up the first side 30, the second side 32, the third side 34 and the fourth side 36 to completely surround the conductive fibre(s) 22. In turn, one or more of the sides 30, 32, 34, 36 (e.g. two) of the wall structure 28 can be connected 26 to the fabric layer of the body 13 including predominantly or completely the fibres 24*b*, thus providing for the insulative structure 20 having the four sides 30, 32, 34, 36 to completely encapsulate the conductive fibre(s) 22 along a length L of the conductive fibre(s) 22. In this example, the fibres 24*b* of the fabric layer of the body 13 do not make up one of the sides 30, 32, 34, 36, other than where used (optionally) for the connections 26 of the wall structure 28 to the fabric layer of the body 13. In either case of FIG. 3 or 6, it is recognised that a cross sectional shape of the wall structure 28 (enclosing the conductive fibre(s) 22 in the cavity 46) can be comprised of sides 30, 32, 34, 36 being rectilinear (e.g. a quadrilateral shape). In either case of FIG.

3 or 7, it is recognised that a cross sectional shape of the wall structure 28 (enclosing the conductive fibre(s) 22 in the cavity 46) can be comprised of sides 30, 32, 34, 36 being arcuate (e.g. a circular shape). In either case of FIG. 3 or 6, it is recognised that a cross sectional shape of the wall structure 28 (enclosing the conductive fibre(s) 22 in the cavity 46) can be comprised of sides 30, 32, 34, 36 being a combination of arcuate and rectilinear.

Figure 7:
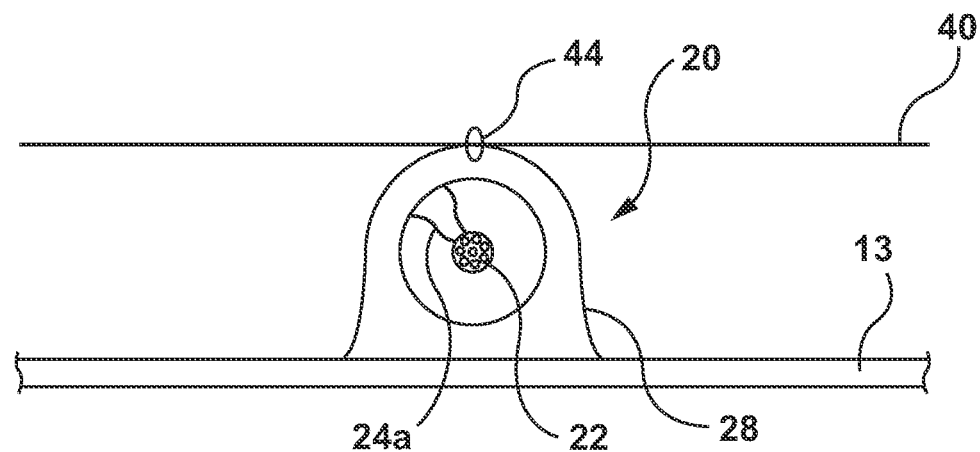
FIG. 7 shows a cross sectional view of a further embodiment of the fibre based temperature sensor of FIG. 3.
Figure 8:
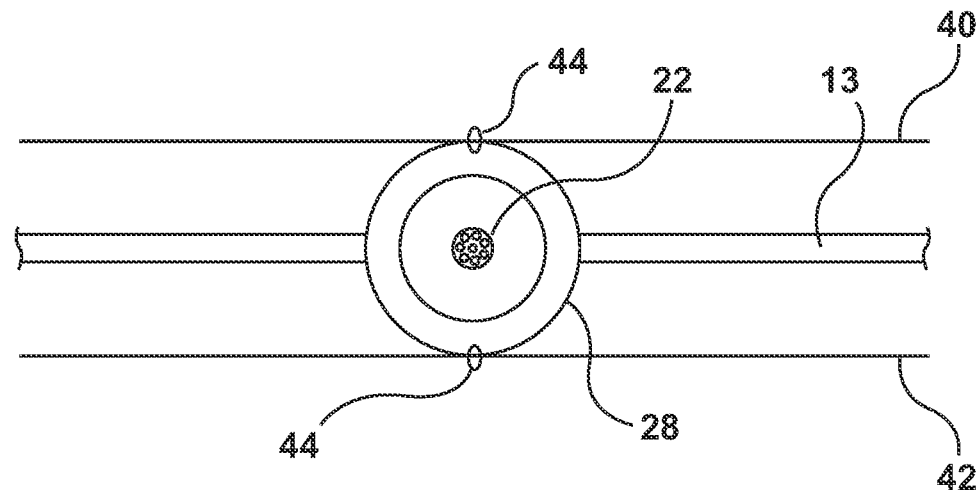
FIG. 8 shows a cross sectional view of a further embodiment of the fibre based temperature sensor of FIG. 3.
Figure 9:
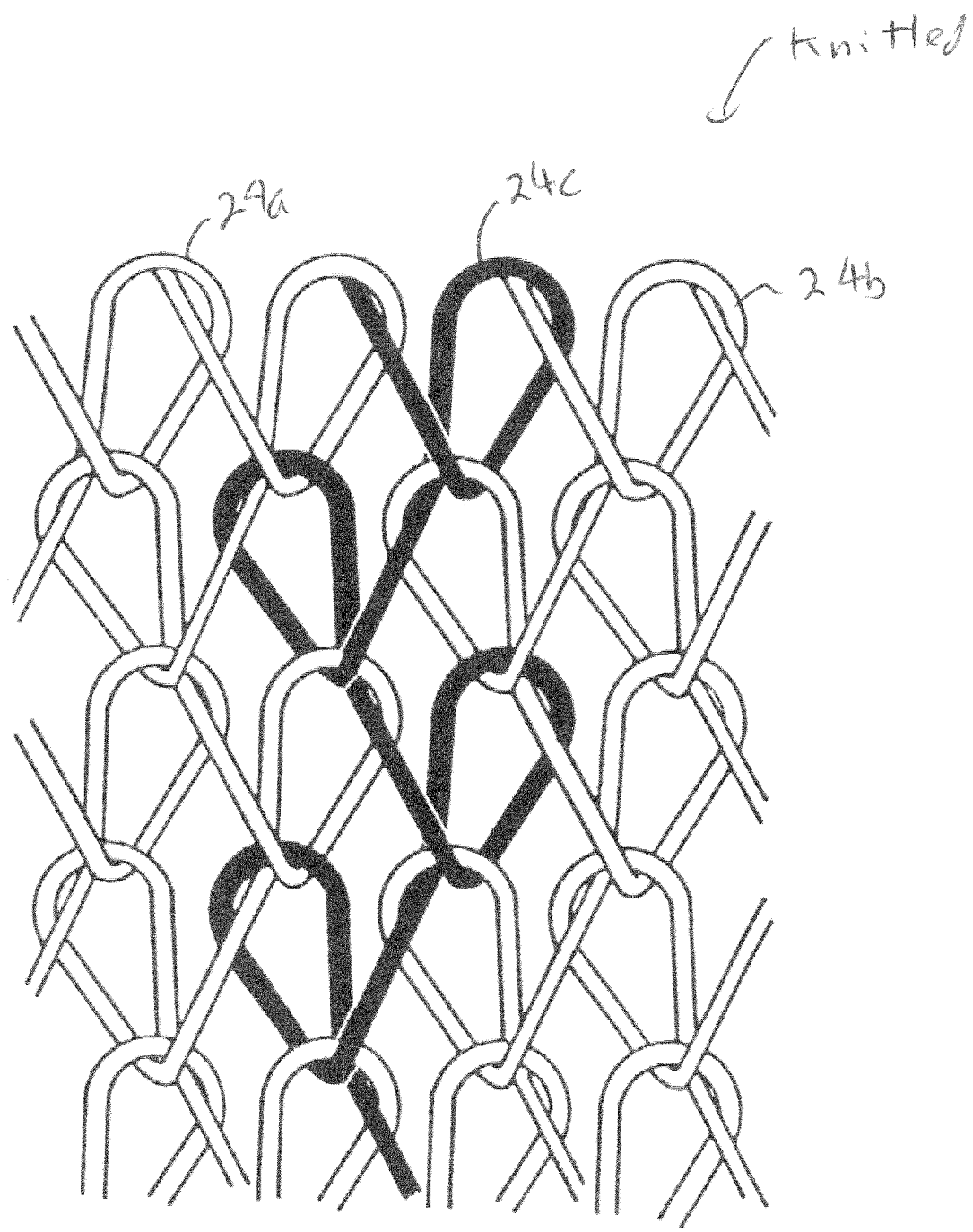
FIG. 9 shows an example technique of interlacing of the fibres of the fibre based temperature sensor connected to fibres in the body of the textile of FIG. 3.

Referring to FIG. 7, shown is an example garment 11 cross section incorporating the insulated conductor 20 having; the wall structure 28 (utilizing a portion of the fabric layer of the body 13), the conductive fibre(s) 22, and a cover fabric layer 40. The cover layer 40 can be used in the garment 11 in order to visually hide the wall structure 28 from observation of the garment wearer. Referring to FIG. 9, shown is a further example garment 11 cross section incorporating the insulated conductor 20 having; the wall structure 28 (utilizing a portion of the fabric layer of the body 13), the conductive fibre(s) 22, the fabric cover layer 40, and a second fabric cover layer 42. The cover layers 40,42 can be used in the garment 11 in order to visually hide the wall structure 28 from observation of the garment wearer.

In terms of the cover layer(s) 40,42, these layer(s) 40,42 can be unconnected, i.e. facilitating any relative movement between the cover layer(s) 40,42 and the wall structure 28 and/or fabric layer of the body 13. Alternatively, these layer(s) 40,42 can be unconnected, such as by using adhesive and/or connecting fibres 44, i.e. inhibiting any relative movement between the cover layer(s) 40,42 and the wall structure 28 and/or fabric layer of the body 13. Further, in terms of the conductive fibre(s) 22, the conductive fibre(s) 22 can be unconnected to any of the fibres 24a,b,c making up the wall structure 28, thereby facilitating relative movement between the sides 30,32,34,36 of the wall structure 28 and the conductive fibre(s) 22. Further, in terms of the conductive fibre(s) 22, the conductive fibre(s) 22 can be connected (e.g. via any one or all of the fibre types 24a, 24b,24c) to any of the fibres 24a,b,c making up the wall structure 28, thereby inhibiting relative movement between the sides 30,32,34,36 of the wall structure 28 and the conductive fibre(s) 22.

The fibres 24a predominantly making up the wall structure 28 can be composed of hydrophilic material, or hydrophilic coated material, in order to inhibit penetration of moisture into the cavity 46 of the wall structure 28 containing the conductive fibre(s) 22. Further, it is recognized that the fibres 24a predominantly making up the wall structure 28 can be comprised of electrically insulative material in order to inhibit undesired transfer of electrical charge between the conductive fibre(s) 22 and the fibres 24b external (i.e. outside of the cavity 46) to the wall structure 28 (e.g. in the fabric layer of the body 13). The material of the conductive fibre(s) 22 can be comprised of a conductive material which has the ability to generate/conduct heat/electricity via the application of a current (or generation of a current) through the conductive fibre(s) 22, i.e. as sensory output/input of the wearer/user implemented by the corresponding application of the device 14,23. For example, the conductive fibre(s) 22 can be made of metal such as silver, stainless steel, copper, and/or aluminum, for example. The non-conductive fibres 24a,24b,24c, which make those portions of the body 13 that contain non-conductive fibres that are not segments in the conductive circuit 17/sensors/actuators 18), can be selected from available synthetic fibers and yarns, such as polyester, nylon, polypropylene, etc., and any equivalent thereof), natural fiber and yarns (such as, cotton, wool, etc., and any equivalent thereof), a combination and/or permutation thereof, and each as required for the final properties of the garment 11 or textile structure 9.

Figure 14A:
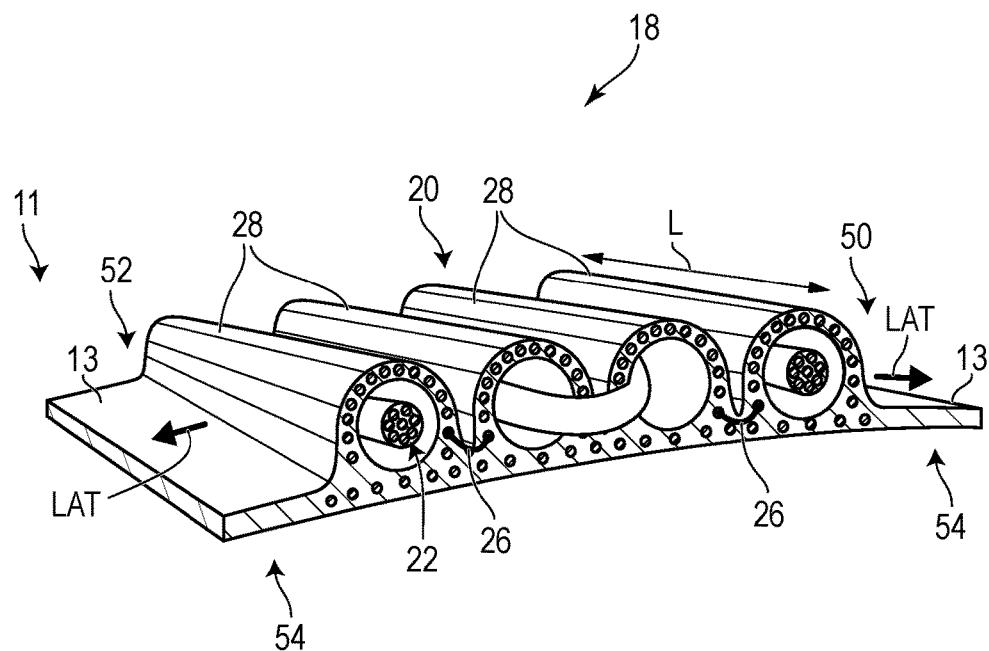
FIG. 14a is a further embodiment of the fibre based temperature sensor of FIG. 3.

Referring to FIG. 14a, shown is an accordion type structure 50 comprising a plurality of wall structures 28 adjacent to one another, as interposed in a section 52 between adjacent body 13 sections 54. The accordion type structure 50 includes the individual wall structures 28 and respective conductive fibre(s) 22 contained within each wall structure 28 along the length L, thereby forming one of the sensors 18 (see FIG. 3). As an example, the sensor 18 can be calibrated to measure the temperature of adjacent objects, e.g. garment/textile 11 wearer's body, external environment to the wearer and the garment/textile 11, measure temperature of the user's body 8 adjacent to the textile 11 (e.g. seat covering, sheet, etc.), etc. As described above, each wall structure 28 comprises fibres 24a interlaced with one another to form the wall structures 28 also interconnected 26 (i.e. interlaced) with the set of fibres 24b making up the surface layer of the body 13 of the textile garment 11 (i.e. adjacent sections 54). It is also recognised that the accordion type structure 50 can extend (e.g. from either one side or both sides—see FIGS. 5 and 6) from the body 13 of the garment 11. It is recognised that the adjacent wall structures 28 are also connected 26 to one another.

Figure 14B:
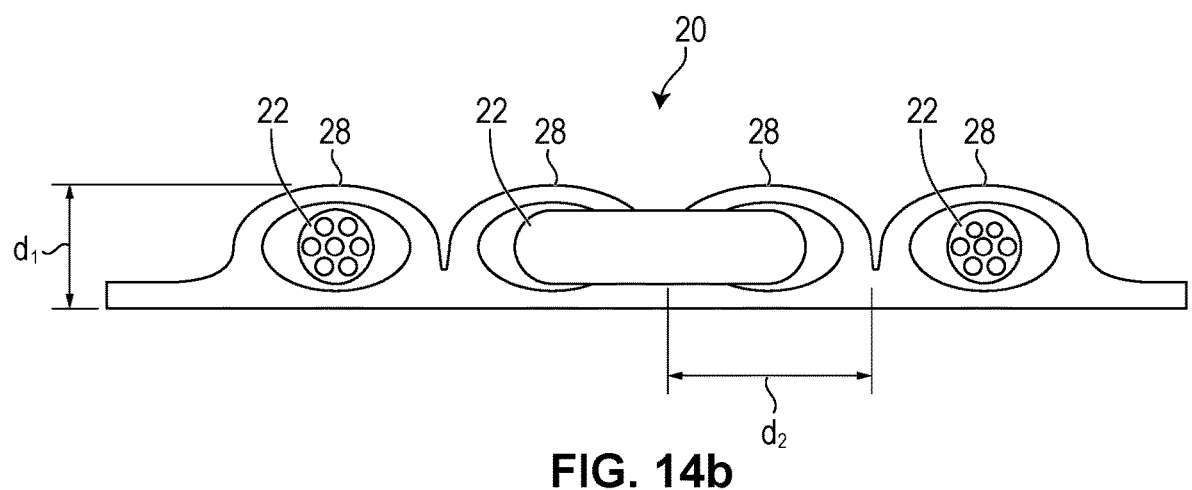

An advantage to the accordion type structure 50 is that the wall structures 28 provide for stretching in a direction LAT laterally (e.g. 90 degrees or other as desired) to the direction/length L of the wall structures 28, such that the respective conductive fibre(s) 22 in each of the wall structures 28 are inhibited from stretching in the L direction while the sensor 18 as a whole is facilitated to stretch and therefore move with the wearer of the garment 11 in the LAT direction. The ability of each of the wall structures 28 as a group in the accordion type structure 50 provides for the senor 18 to stretch along with the adjacent base body 13 sections 54 while at the same time inhibiting any stretch in the individual conductors 22. For example, the cross sectional shape of the wall structures 28 in a pre-stretched configuration (e.g. relaxed state—see FIG. 14a) is circular while the cross sectional shape of the wall structures 28 in a stretched configuration (e.g. stretched state—see FIG. 14b) is more oval. In other words, a dimension D1 of the cross section (lateral to the length L) of the wall structure 28 decreases in size from the relaxed state to the stretched state while a dimension D2 lateral to both D1 and the direction L increases in size from the relaxed state to the stretched state, thus providing for the extendibility or stretch ability of the sensor 18 in the LAT direction while inhibiting any stretch/strain of the individual conductive fibre(s) 22 in the LAT direction.

It is important to note that in the sensor 18 as insulated by the accordion type structure 50, the individual conductors 22 (e.g. conductive fibre(s)) are not interlaced with one another along the length L as the individual conductors are contained within their respective wall structures 28), as compared to the interlacing between the other fibres 24a,c used to make up the wall structures 28 themselves and with the adjacent set of body 13 fibres 24b in the sections 50. It is recognised that the conductors 22 preferably are shielded or otherwise insulated from contact with one another along the respective lengths L of each of the adjacent wall structures 28, i.e. by the presence of the set of interlaced fibres 24a,c making up the sides 30, 32,34,36 of the wall structures 28 (see FIGS. 5,6). As such, the sides 30,32,34,36 of the wall structures 28 form the cavity 46 in which the respective conductive fibre(s) 22 reside or are otherwise contained in order to shield them from moisture and/or electrical shorting with respect to the presence of water and/or other electrically conductive objects/bodies external to the wall structures 28.

Referring to FIGS. 15A,B,C, shown are example embodiments of sensor circuits 58a,58b,58c of the sensors 18, namely a 2 wire, a 3 wire and a 4 wire RTD (Resistance Temperature Detector) temperature sensor circuits. It is noted that the adjacent wall structures 28 (containing interlaced fibres 24a) are connected 26 to one another, for example using connection fibres 24c (however fibres 24b shared in both the wall structure 28 as well as in the adjacent body 13 section 54 could be used as the connection 26, either alone or in combination with the connection fibres 24c). As shown, each of the sensor circuits 58a,b,c have a plurality of conductors 22 (e.g. 2, 3, 4 respectively), each electrically connected at one end 60 to the controller 14 and also connected to one or more of each other (i.e. conductor(s) 22) at the other end 62, such that each end 60,62 are opposed to one another with respect to the length L (see FIG. 5) of the wall structures 28. Accordingly, at end 62, at least a pair of the conductors 22 are electrically connected to one another (e.g. via a detector 64 portion of the circuit 58a,b,c—e.g. representative resistance element of the sensor 58a,b,c). At the other end 60, each of the conductors are electrically connected to the controller 14. It is recognised that each of the conductors 22 are positioned electrically parallel to one another in the circuit 58a,b,c between the endpoints 60,62. Further, the conductors 22 are only electrically connected to one another at the one end 62 and at the other end 60 to the common controller 14. As such, along the length L, the conductors 2 remain electrically insulated from one another in view of the adjacent wall structures 28 making up the accordion type structure 50. It is recognised that the detector element 64 as a representative resistive element could be provided by the resistive value(s) of the conductors 22 in a region of the conductors 22 specified as the temperature sensor 18 (see FIG. 2, such that the remainder portion of the conductor(s) 22 act as the conductive pathway(s) 17.

Figure 16:
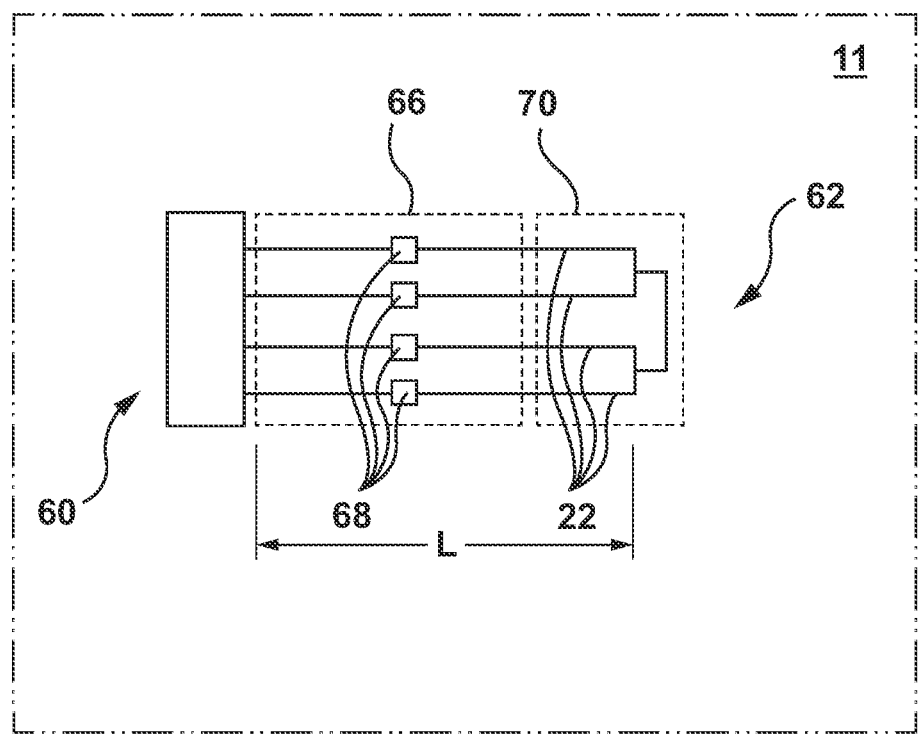

See FIG. 16 showing different portions of the conductors 22 acting as the sensor 18 portion as well as the pathway 17 portion. In this example, the 4 wire conductor 22 embodiment is shown by way of example only. Note, the wall structures 28 (see FIG. 15C) have been omitted for clarity purposes only in FIG. 16. As noted, the portion 66 of the plurality of conductors 22 along the length L provide for electrical conduction of electrical signals 68 between the portion 70 of the plurality of conductors 22 along length L used to sense temperature of an adjacent body part of the wearer of the garment 11 incorporating the sensor 18 (see FIGS. 1, 2), as received and interpreted by the controller 14. It is recognised that as the temperature of the wearer (and/or environment) adjacent to the portion 70 of the conductors 22 is measured, this temperature value is correlated (as interpreted by the controller 14) to the amount of resistivity of the conductors 22, e.g. as the temperature goes up, the resistivity of the conductors 22 as measured by the controller 14 via the signals 68 (e.g. change in current for a constantly applied voltage) goes up. In turn, the resistivity of the portion 70 is correlated to temperature via the applied voltage in the across the circuit 58a,b,c. It is recognised that the resistivity of a conductor increases with temperature. In the case of copper/stainless steel/silver, the relationship between resistivity and temperature is approximately linear over a wide range of temperatures. For other materials, a power relationship can work better. Therefore, it is recognised that resistivity of a conductor increases with temperature and as such the resistivity of the portion 70 (e.g. detector 64 portion) is measured via the pathways 17 in connection with the controller 14.

Figure 17:
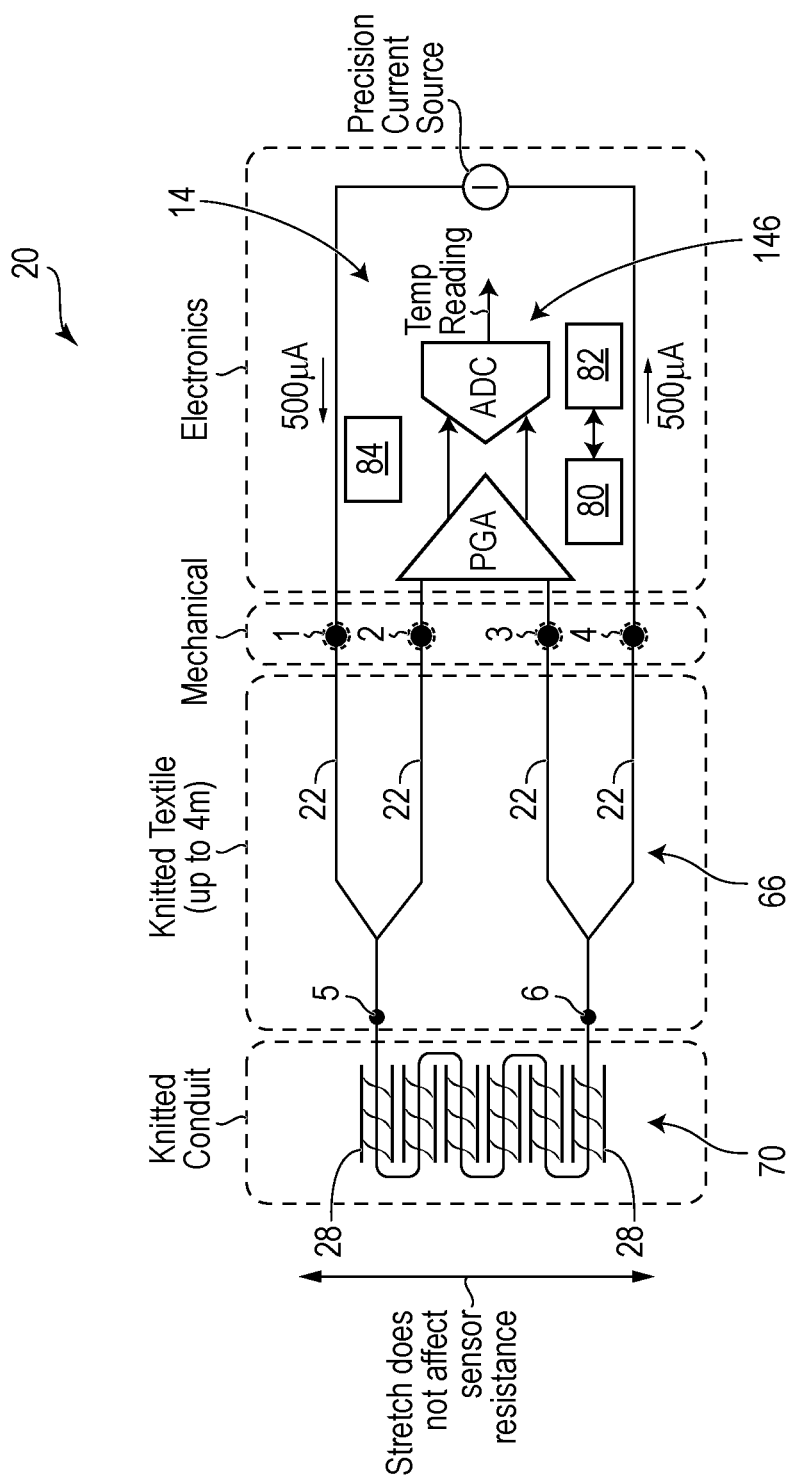

Referring to FIG. 17, shown is an embodiment of the insulated conductor 20 having the wall structure 28 around the multiple conductive fibres 22 in the sensor portion 70 (e.g. detector 64 portion). It is recognised that the resistivity of the conductive fibres 22 in the sensor portion 70 (e.g. detector 64 portion) can be greater than the resistivity of the conductive fibres 22 in the sensor portion 66 (e.g. pathway portion) between the detector portion 64 and the controller 14. In other words, the conductive fibres in the pathway portion 66 are connected at one end to the physical connectors 1,2,3,4 (as the electrical interface to the electronics of the controller 14) and at the other end 5,6 to the detector portion 64. The difference in resistivity in the conductive fibres 22 in the different portions 66,70 can be used to inhibit influence of the conductive fibres 22 in the pathway portion 66 from overly influencing the resistivity (and thus sensitivity) of the temperature detection capabilities of the conductive fibres 22 in the detector portion 64 of circuit portion 70.

Figure 18:
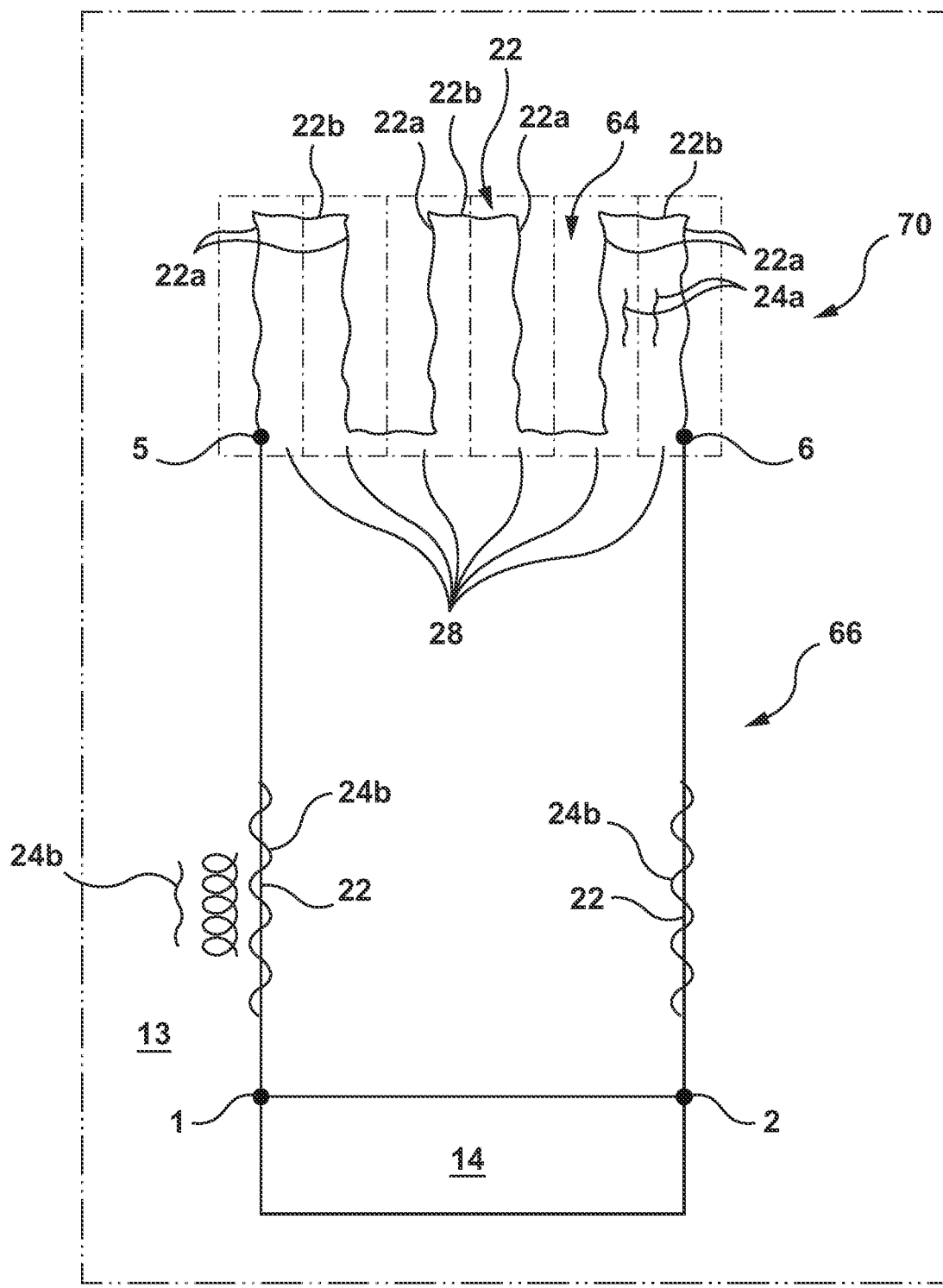

Shown in FIG. 18 is an example in which the detector portion 64 (with multiple conductive fibres 22 side by side) has a respective wall structure 28 (in ghosted view) adjacent to one another for the multiple conductive fibres 22 therein. This is compared to the conductive fibres 22 in the pathway portion 66, which are not within wall structures 28 and thus are not insulated by wall structures 28 and thus can be directly interlaced into the body fibres 24b of the base fabric layer 13 (see FIG. 3). In this example, the resistivity of the conductive fibres 22 in the pathway portion 66 can be less than the resistivity of the conductive fibres 22 in the detector portion 64, for example by a difference in material (i.e. dissimilar materials) of the conductive fibres 22 in the different portions 66,70 and/or differences in cross sectional areas of the conductive fibres 22 between the different portions 66,70.

Figure 19:
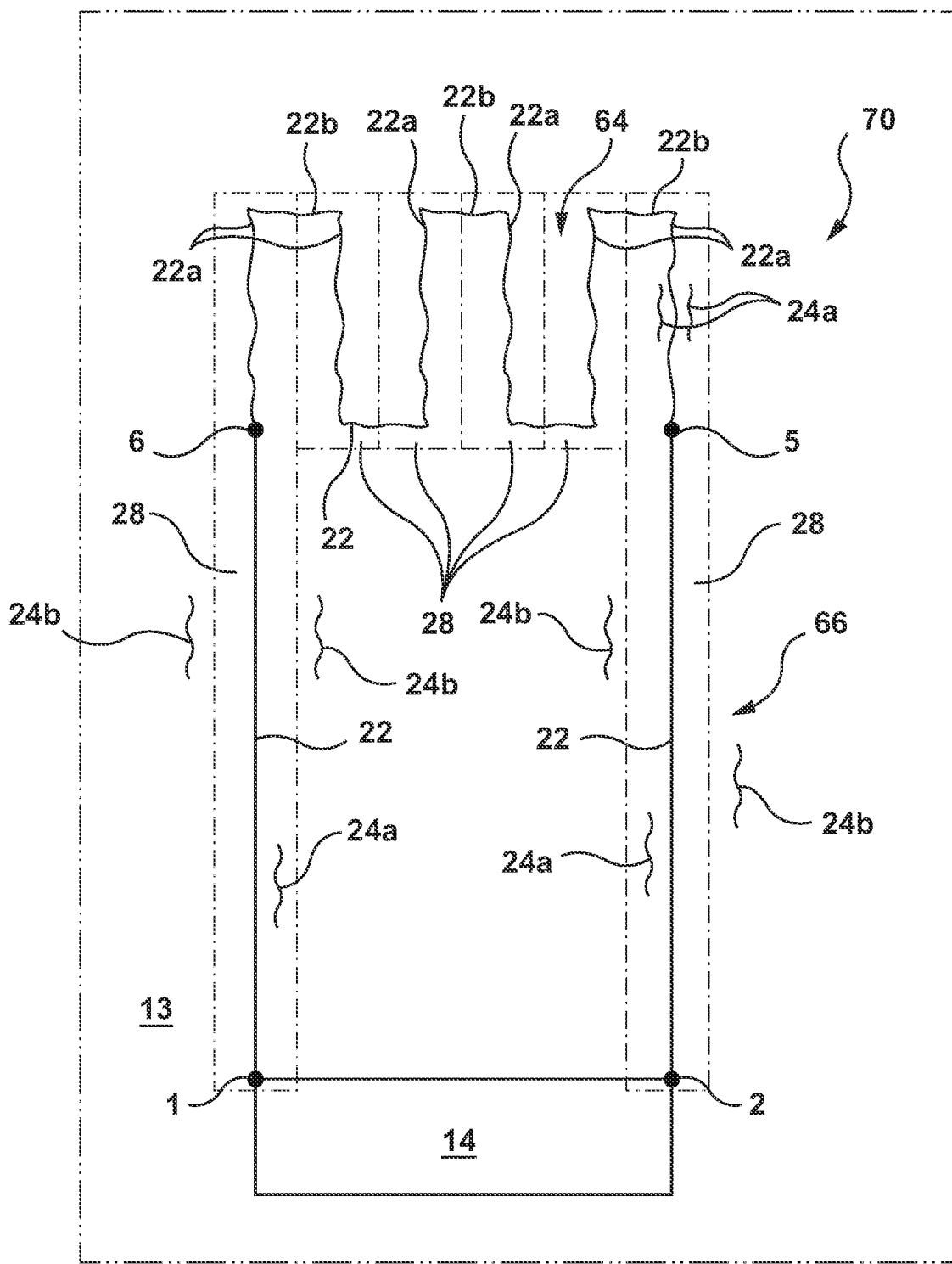

Shown in FIG. 19 is an example in which the detector portion 64 (with multiple conductive fibres 22 side by side) has a respective wall structure 28 (in ghosted view) adjacent to one another for the multiple conductive fibres 22 therein. This is compared to the conductive fibres 22 in the pathway portion 66, which are also within wall structures 28 and thus are also insulated by their wall structures 28 and thus are not directly interlaced into the body fibres 24b of the base fabric layer 13 (see FIG. 3). In this example, the resistivity of the conductive fibres 22 in the pathway portion 66 can be less than the resistivity of the conductive fibres 22 in the detector portion 64, for example by a difference in material (i.e. dissimilar materials) of the conductive fibres 22 in the different portions 66,70 and/or differences in cross sectional areas of the conductive fibres 22 between the different portions 66,70.

Referring again to FIGS. 18 and 19, shown are the multiple segments 22a of the conductive fibre(s) 22 adjacent to one another in the detector portion 64. These segments 22a each run along the length L of their respective wall structure 28 (see FIG. 14a). Also, shown are segments 22b of the conductive fibre(s) 22 interconnecting the various segments 22a. The segments 22b are positioned transverse to the lengths L of the wall structures 28 for the segments 22a, however these segments 22b can also be contained in their own wall structures 28 running transverse (i.e. between adjacent wall structures 28 to the wall structures 28 for the segments 22a). In this manner, for example, the conductive fibre(s) 22 made up of multiple segments 22a,b are insulted within their respective wall structures 28 adjacent to one another.

Referring to FIG. 17, shown is an example of controller electronics 14a use to apply a constant current (I) through the outer connectors, 1 and 4. The voltage drop is measured across the inner connectors, 2 and 3, for example. So from V=IR, the controller 14 can determine the resistance of the detector portion 64. As shown the electronics 14a (e.g. including computer processor 80 and memory 82) can be used to correlate measured resistance with corresponding temperature (e.g. via a stored correlation table), and thus report same to the operator of the controller 14. It is recognised that the electronics 14a would also have a power source 84 for applying the current I to the connectors 1,4. Therefore, each knitted conduit 28 carries an individual conductive yarn strand 22 in the length direction to the location of the temperature sensor (e.g. stainless steel yarns in the detector portion 64). At each end, two of the conductive yarn strands 22 in the pathway portion 70 can be joined together along with one end of the yarn 22. The same is repeated at the other end. This forms the 4-wire temperature sensor. A precision current source of 500 uA of the electronics 14a can be used to measure the resistance using a PGA (programmable Gain Amplifier) and a 24-Bit ADC of the electronics 14a. The resistance can be converted to a voltage and then translated to temperature by the electronics 14a. Calibration may not be necessary as the conductive fibres 22 in the pathway portion are controlled by length upon interlacing or layout within their own wall structure(s) 28. As discussed above, also, the conductive segments 22a, 22b are then in-layered (in their respective wall structures 28) transversely to provide the "accordion" benefit of the structure. This is advantageous as it inhibits the conductive segments 22a,b from stretching but allows the base fabric layer 13 to have significant stretch during active use of the garment/textile 11.

Figure 10:
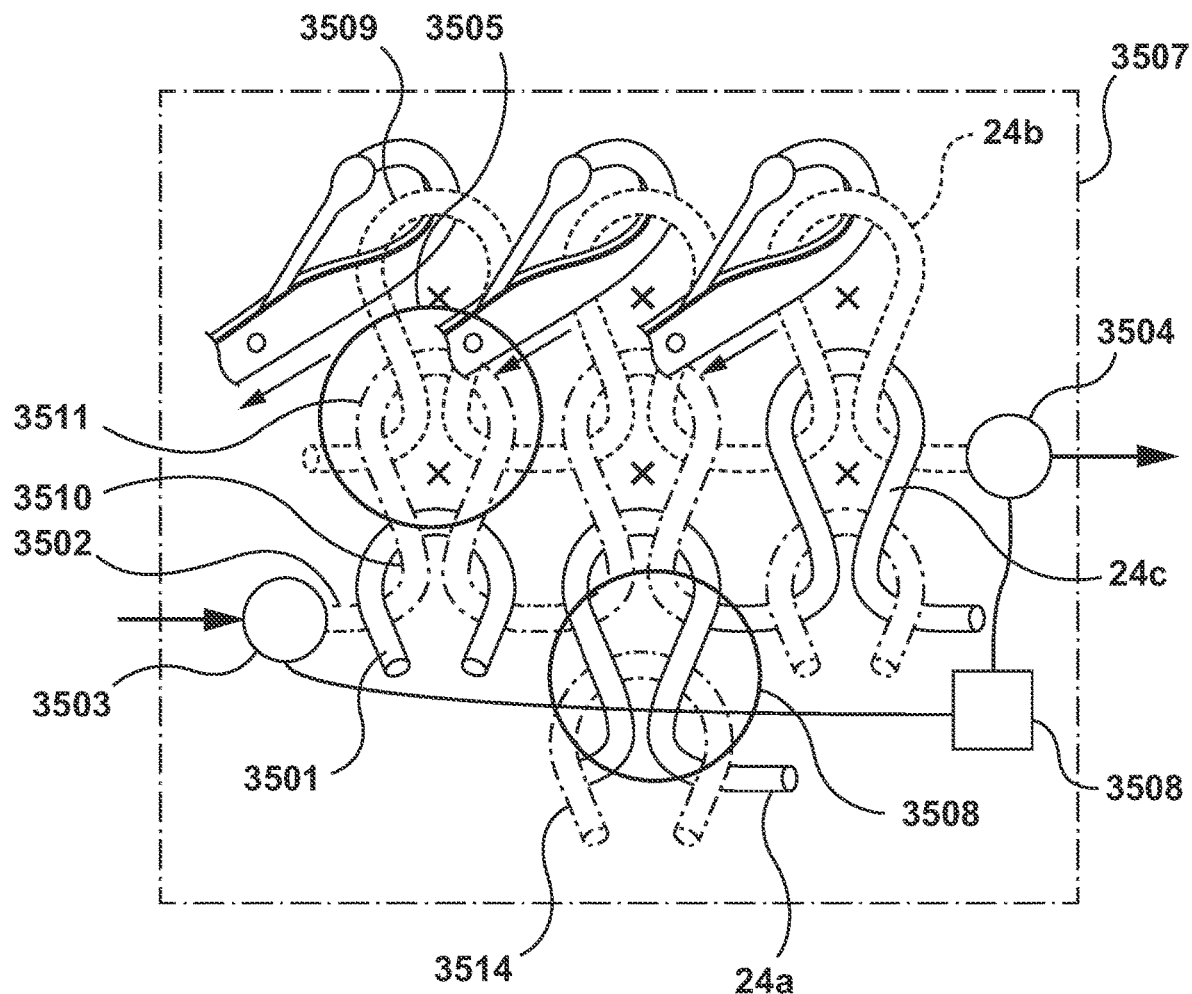
FIG. 10 shows a further example technique of interlacing of fibres for the textile of FIG. 3.
Figure 11:
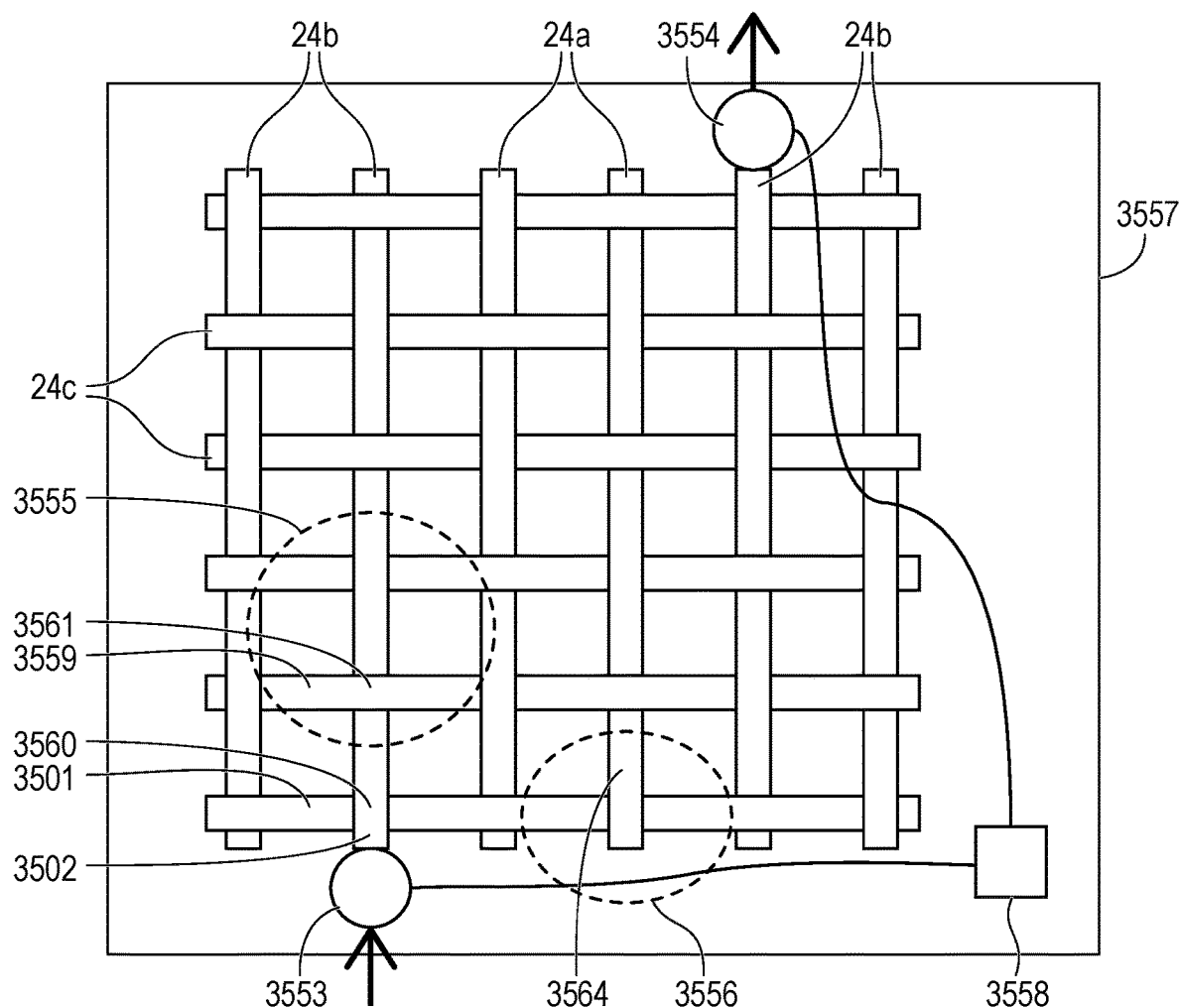
FIG. 11 shows a further example technique of interlacing of the fibres of the fibre based temperature sensor connected to fibres in the body of the textile of FIG. 3.

Referring to FIGS. 2, 9, 10 and 11, in one example embodiment, knitting can be used to integrate different sections of the textile (i.e. body 13 fibres 24b incorporating fibres of the sensors/actuators 18) into a common layer (e.g. having conductive pathway(s) 17 and non-conductive sections). Knitting comprises creating multiple loops of fibre or yarn, called stitches, in a line or tube. In this manner, the fibre or yarn in knitted fabrics follows a meandering path (e.g. a course), forming loops above and below the mean path of the yarn. These meandering loops can be easily stretched in different directions. Consecutive rows of loops can be attached using interlocking loops of fibre or yarn. As each row progresses, a newly created loop of fibre or yarn is pulled through one or more loops of fibre or yarn from a prior row. For example a shown in FIG. 9, warp knitting techniques can be used to integrate different sections of the textile (i.e. body 13 fibres 24b incorporating fibres of the sensors/actuators 18) into a common layer (e.g. having conductive pathway(s) and non-conductive sections). As shown in FIG. 11, weaving can be a further interlacing method of forming a textile in which two distinct sets of yarns or fibres are interlaced at transverse to one another (e.g. right angles) to form a textile.

For example, FIG. 10 shows an exemplary knitted configuration of a network of electrically conductive fibres 3505 in, for example, a segment of an electrically conductive circuit 17 and/or sensor/actuator 18 (see FIG. 1). In this embodiment, an electric signal (e.g. current) is transmitted to conductive fibre 3502 from a power source (not shown) through a first connector 3505, as controlled by a controller 3508 (e.g. controller 14). The electric signal is transmitted along the electric pathway along conductive fibre 3502 past non-conductive fibre 3501 at junction point 3510. The electric signal is not propagated into non-conductive fibre 3501 at junction point 3510 because non-conductive fibre 3501 cannot conduct electricity. Junction point 3510 can refer to any point where adjacent conductive fibres and non-conductive fibres are contacting each other (e.g. touching). In the embodiment shown in FIG. 10, non-conductive fibre 3501 and conductive fibre 3502 are shown as being interlaced by being knitted together. Knitting is only one exemplary embodiment of interlacing adjacent conductive and non-conductive fibres. It should be noted that non-conductive fibres forming non-conductive network 3506 can be interlaced (e.g. by knitting, etc.). Non-conductive network 3506 can comprise non-conductive fibres (e.g. 3501) and conductive fibres (e.g. 3514) where the conductive fibre 3514 is electrically connected to conductive fibres transmitting the electric signal (e.g. 3502). For example, the interlacing method of the fibres in FIG. 10 can be referred to as weft knitting.

In the embodiment shown in FIG. 10, the electric signal continues to be transmitted from junction point 3510 along conductive fibre 3502 until it reaches connection point 3511. Here, the electric signal propagates laterally (e.g. transverse) from conductive fibre 3502 into conductive fibre 3509 because conductive fibre 3509 can conduct electricity. Connection point 3511 can refer to any point where adjacent conductive fibres (e.g. 3502 and 3509) are contacting each other (e.g. touching). In the embodiment shown in FIG. 10, conductive fibre 3502 and conductive fibre 3509 are shown as being interlaced by being knitted together. Again, knitting is only one exemplary embodiment of interlacing adjacent conductive fibres. The electric signal continues to be transmitted from connection point 3511 along the electric pathway to connector 3504. At least one fibre of network 3505 is attached to connector 3504 to transmit the electric signal from the electric pathway (e.g. network 3505) to connector 3504. Connector 3504 is connected to a power source (not shown) to complete the electric circuit.

FIG. 11 shows an exemplary woven configuration of a network of electrically conductive fibres 3555. In this embodiment, an electric signal (e.g. current) is transmitted to conductive fibre 3552 from a power source (not shown) through a first connector 3555, as controlled by a controller 3558 (e.g. controller 14). The electric signal is transmitted along the electric pathway along conductive fibre 3552 past non-conductive fibre 3551 at junction point 3560. The electric signal is not propagated into non-conductive fibre 3551 at junction point 3560 because non-conductive fibre 3551 cannot conduct electricity. Junction point 3560 can refer to any point where adjacent conductive fibres and non-conductive fibres are contacting each other (e.g. touching). In the embodiment shown in FIG. 20, non-conductive fibre 3551 and conductive fibre 3502 are shown as being interlaced by being woven together. Weaving is only one exemplary embodiment of interlacing adjacent conductive and non-conductive fibres. It should be noted that non-conductive fibres forming non-conductive network 3556 are also interlaced (e.g. by weaving, etc.). Non-conductive network 3556 can comprise non-conductive fibres (e.g. 3551 and 3564) and can also comprise conductive fibres that are not electrically connected to conductive fibres transmitting the electric signal. The electric signal continues to be transmitted from junction point 3560 along conductive fibre 3502 until it reaches connection point 3561. Here, the electric signal propagates laterally (e.g. transverse) from conductive fibre 3552 into conductive fibre 3559 because conductive fibre 3559 can conduct electricity. Connection point 3561 can refer to any point where adjacent conductive fibres (e.g. 3552 and 3559) are contacting each other (e.g. touching). In the embodiment shown in FIG. 11, conductive fibre 3552 and conductive fibre 3559 are shown as being interlaced by being woven together. The electric signal continues to be transmitted from connection point 3561 along the electric pathway through a plurality of connection points 3561 to connector 3554. At least one conductive fibre of network 3555 is attached to connector 3554 to transmit the electric signal from the electric pathway (e.g. network 3555) to connector 3554. Connector 3554 is connected to a power source (not shown) to complete the electric circuit. Again, weaving is only one exemplary embodiment of interlacing adjacent conductive fibres, such as fibres 24a,b,c as shown in demonstrating the interlacing technique of weaving the conduit 20 containing the fibres 24a as connected to the body 13 fibres 24b via connecting fibres 24c.

It is recognised that in general, a knit fabric is made up of one or more fibres formed into a series of loops that create rows and columns of vertically and horizontally interconnected stitches. A vertical column of stitches is called a wale, and a horizontal row of stitches is called a course.

In view of FIGS. 3 and 9, the interlacing of the fibres 24a, 24b, 24c (optional) making the insulated conductor 20 in combination with the fabric layer of the body 13 can be provided using knitting as the interlacing method via warp knitting (describing the direction in which the fabric is produced), also referred to as flat knitting, which is a family of knitting methods in which the fibres 24a, 24b, 24c zigzag along the length of the fabric (the combination of the wall structure 28 with the body 13), i.e. following adjacent columns, or wales, of knitting, rather than a single row (also referred to as weft knitting). A warp knit is made with multiple parallel fibres that are simultaneously looped vertically (at the same time) to form the fabric. A warp knit is typically produced on a flat-bed knitting machine, which delivers flat yardage. For example, a "Flat" or Vee Bed knitting machine can consists of 2 flat needle beds arranged in an upside-down "V" formation. These needle beds can be up to 2.5 metres wide. A carriage, also known as a Cambox or Head, moves backwards and forwards across these needle beds, working the needles to selectively, knit, tuck or transfer stitches. The flat knitting machine can provide for complex stitch designs, shaped knitting and precise width adjustment. Again as the name infers, flat bed are horizontal needle beds where the yarn is moved across the vee shaped needle bed within feeders.

For comparison, knitting across the width of the fabric is called weft knitting (also referred to as circular knitting), for example see FIG. 10. Contrary to warp knitting, weft knitting (describing the direction in which the fabric is produced) is such fabric made with a single yarn that's looped to create horizontal rows, or courses, with each row built on the previous row. A weft knits is typically performed on a circular knitting machine, which produces a tube of fabric. For example, circular, as the name infers, is knitting in the round. Here the yarn fed directly [up to 32 separate yarns] into the needle bed that spins around in one direction and creates a tube on fabric through the centre. Simultaneous construction of the desired wall structure 28, in combination with the fabric layer of the body 13, cannot be performed as desired using circular knitting techniques. Accordingly, for interlacing done as knitting, warp knitting is needed to simultaneous construct the desired wall structure 28 in combination with the fabric layer of the body 13

Further, interlacing of the fibres 24a, 24b, 24c (optional) making up the insulated conductor 20 in combination with the fabric layer of the body 13 can be provided using weaving as the interlacing method, which is composed of a series of warp (lengthwise) fibres interlaced with a series of weft (crosswise) fibres. As such, in a woven fabric, the terms warp and weft refer to the direction of the two sets of fibres making up the fabric.

Accordingly, as described above with reference to the figures, a system of an insulated conductor 20 integrated into a base fabric layer 13 for a garment 11, the system comprising: a set of wall fibres 24a interlaced with one another to form a wall structure 18 defining a cavity 46 along a length L, the set of wall fibres 24a comprising nonconductive material; at least one conductive fibre 22 running along the length L within the cavity 46, such that the set of wall fibres 24a of the wall structure 18 encloses the at least one conductive fibre 22 in order to electrically insulate the at least one conductive fibre 22 from an environment 5 along the length L external to the cavity 46; and a set of base fibres 24b interlaced with one another to form the base fabric layer 13, the base fabric layer 13 having a first side 10 adjacent with a first fibred interconnection 26 to the wall structure 18 and a second side 12 adjacent with a second fibered interconnection 26 to the wall structure 18, the first fibered interconnection 26 opposed to the second fibred interconnection 26, the first side 10 and the second side 10 forming a surface of the base fabric layer 13 such that the wall structure 18 is interposed between the first 10 and second 12 sides, the first fibred interconnection 26 and the second fibred interconnection 26 forming part of a structural fabric integrity of the set of wall fibres 24a and a structural fabric integrity of the set of base fibres 24b; wherein damage to fibres of at least one of the first fibred interconnection 26 and the second fibred interconnection 26 results in destruction of the structural fabric integrity of the set of wall fibres 24a and the structural fabric integrity of the set of base fibres 24b.

Figure 12:
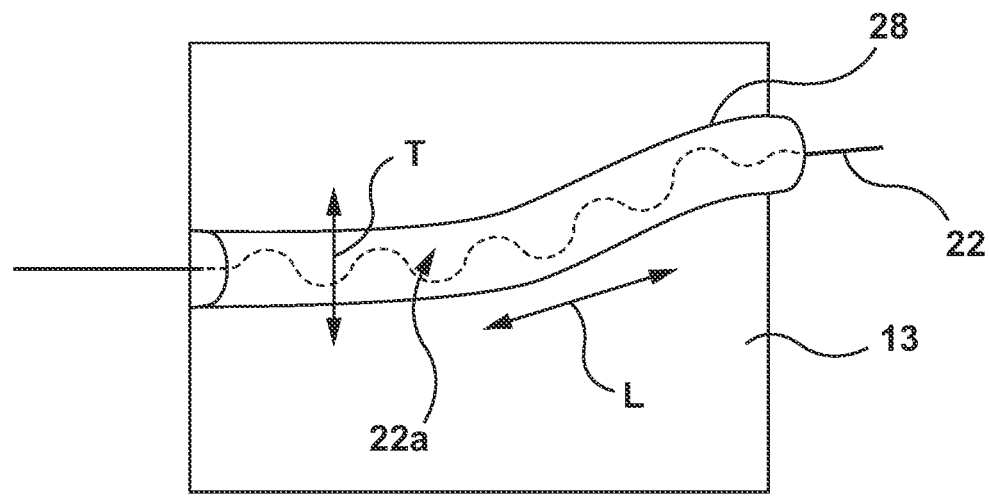
FIG. 12 is an alternative embodiment of the fibre based temperature sensor of FIG. 3.

Referring to FIG. 12, show is the wall structure 28 incorporated into the base fabric layer 13 as described above, i.e. involving the shared structural integrity of both the wall structure 28 interlacing and the base fabric layer 13 interlacing, using one or more pairs of fibre types incorporated in the interlacing of the wall structure 28, e.g. the pair of types of fibres 24a,b, the pair of types of fibres 24a,c, or the two pairs of types of fibres 24a,b and 24a,c (see FIG. 3). The conductive fibre(s) 22 positioned along the length of the wall structure 28 can be oriented in a serpentine fashion, i.e. the length of the conductive fibre(s) 22 within the wall structure 28 is greater that the length of the wall structure 28 itself. For example, the conductive fibre(s) 22 can contain alternating folds 22a in a direction transverse T to the length L of the wall structure 28. These alternating folds 22a can advantageously provide for stretching experienced by the base fabric layer 13 in the length L direction and/or in both the length L and transverse T directions as the garment/textile 11 is utilized by the user/wearer.

Figure 13:
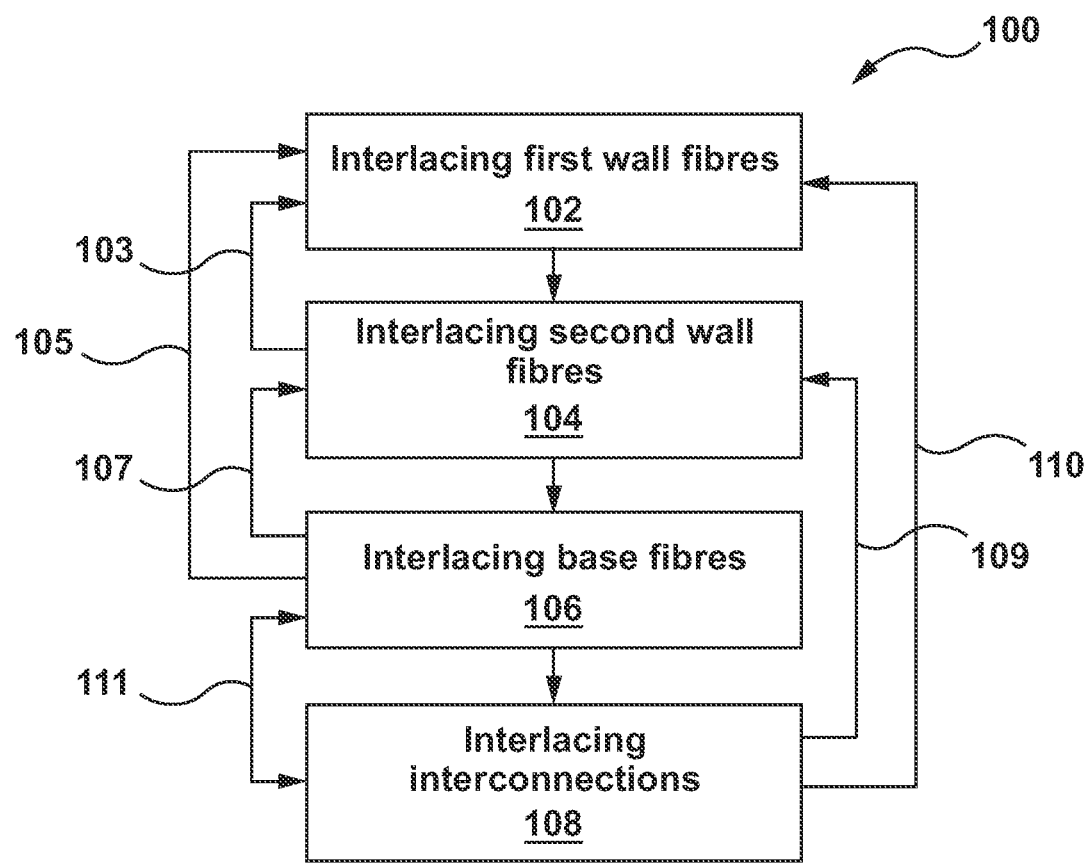
FIG. 13 is an example method of manufacturing the fibre based temperature sensor of FIG. 3.

Referring to FIG. 13, shown is a method 100 for manufacturing an insulated conductor 22 integrated into a base fabric layer 13 for a textile 11, the method comprising the steps of: interlacing 102 a set of first wall fibres 24a with one another to form a first wall structure 28 defining a cavity 46 along a length L, the set of first wall fibres 24a comprising nonconductive material; positioning at least one conductive first fibre 22 running along the length L within the cavity 46, such that the set of first wall fibres of the first wall structure 28 encloses the at least one conductive first fibre 22 in order to electrically insulate the at least one conductive first fibre 22 from an environment along the length L external to the cavity 46; interlacing 104 a set of second wall fibres 24a with one another to form a second wall structure 28 defining a cavity 46 along a length L, the set of second wall fibres 24a comprising nonconductive material; positioning 104 at least one conductive second fibre 22 running along the length L within the cavity 46, such that the set of second wall fibres of the second wall structure 28 encloses the at least one conductive second fibre 22 in order to electrically insulate the at least one conductive second fibre 22 from an environment along the length L external to the cavity 46; interlacing 106 a set of base fibres 24b with one another to form the base fabric layer 13; and interlacing 108 a first fibred interconnection 26 and a second fibred interconnection 26, the base fabric layer 13 having a first side 10 adjacent with the first fibred interconnection 26 to the first wall structure 28 and a second side 12 adjacent with the second fibered interconnection 26 to the second wall structure 28, the first fibered interconnection 26 opposed to the second fibred interconnection 26, the first side and the second side forming a surface of the base fabric layer 13 such that the first and second wall structures 28 are interposed between the first 10 and second 12 sides, the first fibred interconnection 26 and the second fibred interconnection 26 respectively forming part of a structural fabric integrity of the set of first and second wall 24a fibres and a structural fabric integrity of the set of base 24b fibres; wherein subsequent damage to fibres of at least one of the first fibred interconnection 26 or the second fibred interconnection 26 results in destruction of the structural fabric integrity of the set of first/second wall fibres 24a and the structural fabric integrity of the set of base fibres 24b.

The method 100, wherein the interlacing 102 of the first wall fibres 24a continues 103 after the interlacing 104 of the second wall fibres 24a. The method 100, wherein the interlacing of the first wall fibres 24a continues 105 after the interlacing 104 of the base fibres 24b. The method 100, wherein the interlacing 104 of the second wall fibres 24a continues 107 after the interlacing 104 of the base fibres 24b. The method 100, wherein the interlacing 102 of the first/second wall fibres 24a continues 109,110 after the interlacing 108 of at least one of the first fibred interconnection 26 or the second fibred interconnection 26. The method 100, wherein the interlacing 106 of the base fibres 24b continues 111 after the interlacing 108 of at least one of the first fibred interconnection 26 or the second fibred interconnection 26.

We claim:

1. A system for a fibre based temperature sensor integrated into a base fabric layer for a textile, the system comprising:
    a first set of wall fibres interlaced with one another to form a first wall structure defining a first cavity along a length, the first set of wall fibres comprising nonconductive material;
    at least one conductive first fibre running along the length within the first cavity, such that the first set of wall fibres of the first wall structure encloses the at least one conductive first fibre in order to electrically insulate the at least one conductive first fibre from an environment along the length external to the first cavity;
    a second set of wall fibres interlaced with one another to form a second wall structure defining a second cavity along the length, the second set of wall fibres comprising nonconductive material, the wall structures adjacent to one another along the length;
    at least one conductive second fibre running along the length within the second cavity, such that the second set of wall fibres of the second wall structure encloses the at least one conductive second fibre in order to electrically insulate the at least one conductive second fibre from the environment along the length external to the second cavity, wherein the first wall structure and the second wall structure are adjacent and interconnected to one another;
    a set of base fibres interlaced with one another to form the base fabric layer, the base fabric layer having a first side adjacent with a first fibred interconnection to the first wall structure and a second side adjacent with a second fibered interconnection to the second wall structure, the first fibered interconnection opposed to the second fibred interconnection, the first side and the second side forming a surface of the base fabric layer such that the first wall structure and the second wall structure are interposed between the first and second sides, the first fibred interconnection and the second fibred interconnection forming part of a structural fabric integrity of the set of first wall fibres and the set of second wall fibres respectively in combination with a structural fabric integrity of the set of base fibres;
    wherein damage to fibres of at least one of the first fibred interconnection results in destruction of the structural fabric integrity of the set of first wall fibres or the second fibred interconnection results in destruction of the structural fabric integrity of the set of second wall fibres, in combination with the structural fabric integrity of the set of base fibres.

2. The system of claim 1 further comprising a controller electrically connected to the first conductive fibre and to the second conductive fibre and for measuring a resistivity of the first conductive fibre and the second conductive fibre in order to determine a temperature associated with an object adjacent to the fibre based temperature sensor.

3. The system of claim 1, wherein a material of the at least one conductive fibre is stainless steel.

4. The system of claim 1, wherein the first wall structure includes a plurality of sides defining the cavity, such that one of the sides of the plurality of sides is predominantly formed from base fibres of the set of base fibres, such that the base fibres forming said one of the sides are interlaced with wall fibres of the set of first wall fibres in other walls of the plurality of walls adjacent to said one of the sides.

5. The system of claim 1 further comprising a cover layer spaced apart from the base fabric layer at least adjacent to the first wall structure and the second wall structure, such that the first wall structure and the second wall structure are interposed between the base fabric layer and the cover layer.

6. The system of claim 1, wherein fibres of the first fibred interconnection are interlaced by warp knitting with respect to the adjacent set of first wall fibres and the adjacent base fibres.

7. The system of claim 6, wherein fibres of the second fibred interconnection are interlaced by warp knitting with respect to the adjacent set of second wall fibres and the adjacent base fibres.

8. The system of claim 1 further comprising a length of the at least one conductive first fibre and a length of the at least one conductive second fibre being exposed to the environment and electrically connected to an electrical contact node.

9. The system of claim 1, wherein the set of first wall fibres and the set of second wall fibres are composed of the nonconductive material which is also hydrophilic.

10. The system of claim 1 further comprising a pathway portion and a detector portion of the fibre based temperature sensor, such that the first wall structure and the second wall structure are in the detector portion, wherein the pathway portion is positioned between a controller and the detector portion, a plurality of conductive fibres in the pathway portion connecting the at least one conductive first fibre and the at least one conductive second fibre with the controller, the plurality of conductive fibres interlaced with the base fibres in the base fabric layer of the pathway portion.

11. The system of claim 1 further comprising a pathway portion and a detector portion of the fibre based temperature sensor, such that the first wall structure and the second wall structure are in the detector portion, wherein the pathway portion is positioned between a controller and the detector portion, a plurality of conductive fibres in the pathway portion connecting the at least one conductive first fibre and the at least one conductive second fibre with the controller, the plurality of conductive fibres also situated within their own respective wall structure connected to the base fibres in the base fabric layer of the pathway portion.

12. The system of claim 1 further comprising a conductive fibre segment running transverse to the length between the at least one conductive first fibre and the at least one conductive second fibre, the conductive fibre segment forming part of a detector portion of the fibre based temperature sensor.

13. The system of claim 12, wherein the conductive fibre segment is contained within a respective wall structure running transverse between the first wall structure and the second wall structure.

14. A method for manufacturing fibre based temperature sensor integrated into a base fabric layer for a textile, the method comprising the steps of:
    interlacing a set of wall fibres with one another to form a first wall structure defining a first cavity along a length and a second wall structure defining a second cavity along the length, the set of wall fibres comprising nonconductive material, the wall structures adjacent to one another along the length;
    positioning at least one conductive fibre running along the length within each of the first cavity and the second cavity, such that the set of wall fibres of the wall structures enclose each of the at least one conductive fibre in order to electrically insulate each of the at least one conductive fibre from an environment along the length external to the cavities;
    interlacing a set of base fibres with one another to form the base fabric layer; and interlacing a first fibred interconnection and a second fibred interconnection between the base fabric layer and the first and second wall structures, the base fabric layer having a first side adjacent with the first fibred interconnection to the first wall structure and a second side adjacent with the second fibred interconnection to the second wall structure, the first fibred interconnection opposed to the second fibred interconnection, the first side and the second side forming a surface of the base fabric layer such that the first and second wall structures are interposed between the first and second sides, the first fibred interconnection and the second fibred interconnection forming part of a structural fabric integrity of the set of wall fibres and a structural fabric integrity of the set of base fibres;
    wherein subsequent damage to fibres of at least one of the first fibred interconnection or the second fibred interconnection results in destruction of the structural fabric integrity of the set of wall fibres and the structural fabric integrity of the set of base fibres.

15. A method for manufacturing fibre based temperature sensor integrated into a base fabric layer for a textile, the method comprising the steps of: interlacing a set of wall fibres with one another to form a first wall structure defining a first cavity along a length and a second wall structure defining a second cavity along the length, the set of wall fibres comprising nonconductive material, the wall structures adjacent to one another along the length; positioning at least one conductive fibre running along the length within each of the first cavity and the second cavity, such that the set of wall fibres of the wall structures enclose each of the at least one conductive fibre in order to electrically insulate each of the at least one conductive fibre from an environment along the length external to the cavities; and interlacing a set of base fibres with one another to form the base fabric layer and connected to the pair of first and second wall structures.

16. The method of claim 15 further comprising interlacing a first fibred interconnection and a second fibred interconnection between the base fabric layer and the first and second wall structures, the base fabric layer having a first side adjacent with the first fibred interconnection to the first wall structure and a second side adjacent with the second fibred interconnection to the second wall structure, the first fibred interconnection opposed to the second fibred interconnection, the first side and the second side forming a surface of the base fabric layer such that the first and second wall structures are interposed between the first and second sides, the first fibred interconnection and the second fibred interconnection forming part of a structural fabric integrity of the set of wall fibres and a structural fabric integrity of the set of base fibres; wherein subsequent damage to fibres of at least one of the first fibred interconnection or the second fibred interconnection results in destruction of the structural fabric integrity of the set of wall fibres and the structural fabric integrity of the set of base fibres.

* * * * *